(12) United States Patent
Sang et al.

(10) Patent No.: US 11,839,777 B2
(45) Date of Patent: Dec. 12, 2023

(54) MEDICAL SYSTEMS INCLUDING A POSITIONING LAMP AND A PROJECTION DEVICE AND CONTROL METHODS OF THE MEDICAL SYSTEMS

(71) Applicant: SHANGHAI UNITED IMAGING HEALTHCARE CO., LTD., Shanghai (CN)

(72) Inventors: Shenghua Sang, Shanghai (CN); Xinyue Zhou, Shanghai (CN); Yangyang Lin, Shanghai (CN); Yiqi Huang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 117 days.

(21) Appl. No.: 17/447,933

(22) Filed: Sep. 17, 2021

(65) Prior Publication Data
US 2022/0088413 A1    Mar. 24, 2022

(30) Foreign Application Priority Data

Sep. 21, 2020  (CN) .......................... 202010994668.8
Sep. 23, 2020  (CN) .......................... 202022100024.8

(51) Int. Cl.
*A61B 6/00*    (2006.01)
*A61B 6/03*    (2006.01)
(Continued)

(52) U.S. Cl.
CPC ............ *A61N 5/1049* (2013.01); *A61B 6/032* (2013.01); *A61B 6/035* (2013.01); *A61B 6/037* (2013.01);
(Continued)

(58) Field of Classification Search
CPC ......... A61B 6/032; A61B 6/035; A61B 6/037; A61B 6/04; A61B 6/0407; A61B 6/0487;
(Continued)

(56) References Cited

U.S. PATENT DOCUMENTS 6,990,175 B2 * 1/2006 Nakashima ............ A61B 6/032
                                                    378/92
7,113,569 B2 * 9/2006 Okumura ............... A61B 6/466
                                                    378/150
(Continued)

FOREIGN PATENT DOCUMENTS

CN        1567082 A      1/2005
CN      102908161 A      2/2013
(Continued)

OTHER PUBLICATIONS

Wang, Zhimin et al., Practical Imaging Techniques and Diagnosis, Xi'an Jiaotong University Press, 2018, 5 pages.

*Primary Examiner* — Allen C. Ho
(74) *Attorney, Agent, or Firm* — METIS IP LLC

(57) ABSTRACT

The present disclosure relates to a medical system. The medical system may determine a working phase of the medical system. The working phase of the medical system may include a positioning phase, a scanning phase, and/or a scanning completion phase. The medical system may determine a position of a target portion of an object in the medical system based on one or more images associated with the object captured by an imaging sensor. The medical system may further control an operation of a positioning lamp of the medical system based on the working phase of the medical system and the position of the target portion of the object in the medical system.

20 Claims, 13 Drawing Sheets

(51) Int. Cl.
*A61B 6/04* (2006.01)
*A61B 6/08* (2006.01)
*A61N 5/10* (2006.01)

(52) U.S. Cl.
CPC .............. *A61B 6/04* (2013.01); *A61B 6/0407* (2013.01); *A61B 6/0487* (2020.08); *A61B 6/4258* (2013.01); *A61B 6/46* (2013.01); *A61B 6/461* (2013.01); *A61B 6/462* (2013.01); *A61B 6/467* (2013.01); *A61B 6/469* (2013.01); *A61B 6/488* (2013.01); *A61B 6/5294* (2013.01); *A61N 2005/1056* (2013.01); *A61N 2005/1059* (2013.01)

(58) Field of Classification Search
CPC ....... A61B 6/44; A61B 6/4429; A61B 6/4435; A61B 6/4441; A61B 6/4447; A61B 6/4476; A61B 6/4494; A61B 6/46; A61B 6/461; A61B 6/462; A61B 6/467; A61B 6/469; A61B 6/5294; A61B 6/42; A61B 6/4208; A61B 6/4258; A61B 6/488; A61B 6/54; A61B 6/541; A61B 6/542; A61B 6/544; A61B 6/545; A61N 5/10; A61N 5/103; A61N 5/1048; A61N 5/1049; A61N 2005/1052; A61N 2005/1054; A61N 2005/1056; A61N 2005/1059; A61N 2005/1061; A61N 2005/1062; A61N 2005/1074; A61N 5/1037
USPC ....... 378/62, 65, 98, 165, 166, 205, 206, 63, 378/95
See application file for complete search history.

(56) References Cited

U.S. PATENT DOCUMENTS

| | | | | |
|---|---|---|---|---|
| 7,720,196 | B2 * | 5/2010 | Zhang | A61B 6/4458 |
| | | | | 378/65 |
| 8,611,496 | B2 * | 12/2013 | Terunuma | A61N 5/1049 |
| | | | | 378/65 |
| 10,321,880 | B2 * | 6/2019 | Lerch | A61B 6/462 |
| 10,424,118 | B2 * | 9/2019 | Hannemann | A61B 6/032 |
| 10,687,778 | B2 * | 6/2020 | Lerch | G01R 33/30 |
| 10,789,498 | B2 * | 9/2020 | Cao | A61B 5/1077 |
| 10,857,391 | B2 * | 12/2020 | Stahl | A61B 6/0492 |
| 11,020,022 | B2 * | 6/2021 | Hao | A61B 6/04 |
| 11,182,927 | B2 * | 11/2021 | Hu | G06T 7/80 |
| 11,207,035 | B2 * | 12/2021 | Eibenberger | G16H 50/30 |
| 11,235,176 | B2 * | 2/2022 | Wang | G03H 1/2249 |
| 11,311,266 | B2 * | 4/2022 | Maltz | A61B 6/541 |
| 11,443,441 | B2 * | 9/2022 | Berlinger | A61N 5/1049 |
| 11,510,629 | B2 * | 11/2022 | Pautsch | A61B 5/7207 |
| 11,540,801 | B2 * | 1/2023 | Wu | A61B 6/102 |
| 11,567,149 | B2 * | 1/2023 | Xin | G16H 30/40 |
| 11,612,762 | B2 * | 3/2023 | Hale | H04N 13/25 |
| | | | | 600/1 |
| 11,638,840 | B2 * | 5/2023 | Vojan | A61N 5/1049 |
| | | | | 378/65 |
| 11,672,496 | B2 * | 6/2023 | Liu | G06V 40/10 |
| | | | | 382/131 |

FOREIGN PATENT DOCUMENTS

| | | |
|---|---|---|
| CN | 203914938 U | 11/2014 |
| CN | 109009248 A | 12/2018 |
| CN | 109428991 A | 3/2019 |
| CN | 109924999 A | 6/2019 |
| CN | 111144371 A | 5/2020 |
| JP | S63272329 A | 11/1988 |
| JP | 2001346793 A | 12/2001 |
| JP | 2002360558 A | 12/2002 |
| JP | 2009106572 A | 5/2009 |
| JP | 2009247391 A | 10/2009 |
| JP | 2009254445 A | 11/2009 |

\* cited by examiner

MEDICAL SYSTEMS INCLUDING A POSITIONING LAMP AND A PROJECTION DEVICE AND CONTROL METHODS OF THE MEDICAL SYSTEMS

CROSS-REFERENCE TO RELATED APPLICATIONS

This application claims priority to Chinese Patent Application No. 202010994668.8 filed on Sep. 21, 2020 and Chinese Patent Application No. 202022100024.8 filed on Sep. 23, 2020, the contents of each of which are incorporated herein by reference in their entirety.

TECHNICAL FIELD

The present disclosure generally relates to medical technology, and more particularly, relates to medical systems and control methods of the medical systems.

BACKGROUND

Medical systems, such as a computed tomography (CT) system, a magnetic resonance imaging (MRI) system, a positron emission tomography (PET) system, a radiotherapy (RT) system, etc. are widely used in disease diagnosis and/or treatment for various medical conditions (e.g., tumors, coronary heart diseases, or brain disease). Conventionally, before an object (e.g., a patient or a portion thereof) is performed a medical procedure (e.g., observation, treatment), with the assistance of a user (e.g., a doctor, a radiologist, a nurse), the object may be placed on a table in the required posture and moved to a desired position in a detection region for performing the medical procedure.

SUMMARY

An aspect of the present disclosure relates to a medical system. The medical system may determine a working phase of the medical system. The working phase of the medical system may include a positioning phase, a scanning phase, and/or a scanning completion phase. The medical system may determine a position of a target portion of an object in the medical system based on one or more images associated with the object captured by an imaging sensor. The medical system may further control an operation of a positioning lamp of the medical system based on the working phase of the medical system and the position of the target portion of the object in the medical system.

In some embodiments, the determining the working phase of the medical system may include obtaining workflow information of the medical system in a current medical procedure of an object and determining the working phase of the medical system based on the workflow information of the medical system in the current medical procedure of the object.

In some embodiments, the determining the position of the target portion of the object in the medical system based on the one or more images associated with the object captured by the imaging sensor may include identifying the target portion of the object from the one or more images associated with the object; obtaining a position of the target portion of the object in a first coordinate system of the imaging sensor or the one or more images; and determining the position of the target portion of the object in a second coordinate system of the medical system based on the position of the target portion of the object in the first coordinate system of the imaging sensor or the one or more images.

In some embodiments, the controlling the operation of the positioning lamp of the medical system based on the working phase of the medical system and the position of the target portion of the object in the medical system may include determining whether the working phase of the medical system is the positioning phase; and controlling, in response to determining that the working phase of the medical system is the positioning phase, the operation of the positioning lamp of the medical system based on an irradiation region of the positioning lamp and the position of the target portion of the object in the medical system.

In some embodiments, the determining whether the working phase of the medical system is the positioning phase may include obtaining the one or more images associated with the object, the one or more images including one or more first images of the object and one or more second images of the object and a target object; determining whether the object is located on a table of the medical system based on the one or more first images of the object; determining, in response to determining that the object is located on the table, whether a distance between the table and the target object is less than or equal to a preset threshold based on the one or more second images; and determining, in response to determining that the distance between the table and the target object is less than or equal to the preset threshold, that the working phase of the medical system is the positioning phase.

In some embodiments, the controlling the operation of the positioning lamp of the medical system based on the irradiation region of the positioning lamp and the position of the target portion of the object in the medical system may include determining whether the position of the target portion of the object is within the irradiation region of the positioning lamp; controlling, in response to determining that the position of the target portion of the object is not within the irradiation region of the positioning lamp, the positioning lamp of the medical system to be turned on; and controlling, in response to determining that the position of the target portion of the object is within the irradiation region of the positioning lamp, the positioning lamp of the medical system to keep turned off.

In some embodiments, the controlling, in response to determining that the position of the target portion of the object is not within the irradiation region of the positioning lamp, the positioning lamp of the medical system to keep turned on may include controlling the positioning lamp of the medical system to be turned on based on a position or a movement state of a table of the medical system.

In some embodiments, the controlling the operation of the positioning lamp of the medical system based on the working phase of the medical system and the position of the target portion of the object in the medical system may include controlling, in response to determining that the working phase of the medical system is not the positioning phase, the positioning lamp of the medical system to keep turned off.

In some embodiments, the medical system may further include a radiation device and a projection device. The radiation device may be configured to perform a medical procedure on an object by emitting radiation beams toward the object. The projection device may be configured to project reference image data associated with the object to a target position. The reference image data may provide guidance information associated with the medical procedure for the object. The at least one processor may be in communication with the radiation device and the projection device and configured to control at least one of the radiation device or the projection device.

In some embodiments, the medical system may further include a table configured to move the object placed on the table to a target region for performing the medical procedure. A projection direction of the reference image data projected by the projection device may be perpendicular to a surface of the table for placing the object.

In some embodiments, the medical system may further include a position detection device in communication with the at least one processor. The position detection device may be configured to detect a position of the table. The at least one processor may be configured to determine whether the projection device is triggered to project the reference image data based on the position of the table.

In some embodiments, the medical system may further include a gravity detection device in communication with the at least one processor. The gravity detection device may be configured to detect a weight carried by the table. The at least one processor may be configured to determine whether the projection device is triggered to project the reference image data based on the weight carried by the table.

In some embodiments, the medical system may further include a voice device configured to broadcast the guidance information provided by the reference image data projected by the projection device. The guidance information may include position and posture information that the object needs to maintain on a table of the medical system.

In some embodiments, the imaging sensor may be in communication with the at least one processor. The imaging sensor may be configured to capture one or more images associated with the object. The at least one processor may be configured to notify, by the voice device, the object to perform positioning correction based on a comparison of the one or more images associated with the object and the reference image data.

In some embodiments, the at least one processor may include a trigger component configured to trigger the projection device to project the reference image data to the target position.

In some embodiments, the at least one processor may be further configured to obtain characteristic information of the object. The characteristic information may include age, height, weight, and/or gender of the object. The at least one processor may be further configured to determine the reference image data based on the characteristic information of the object and a trained image data construction model.

In some embodiments, the projection device may further include a receiver, a reconstruction component, and a projection component. The receiver may be configured to receive a projection instruction and projection information from the at least one processor. The projection information may include projection data and a projection angle associated with the reference image data. The reconstruction component may be configured to generate the reference image data based on the projection data. The projection component may be configured to project the reference image data based on the projection instruction and the projection angle.

In some embodiments, the at least one processor may be further configured to determine a target region where a target part of the object that needs to be performed the medical procedure is located based on the reference image data.

A further aspect of the present disclosure relates to a method for controlling a medical system. The medical system may include a table configured to move an object placed on the table and a gantry configured to form a cavity, the gantry being provided with a positioning lamp. The method may include controlling the positioning lamp to be turned on; controlling the table that carries the object to move along a long axis of the cavity to enter the cavity; determining a position of a target portion of the object in the medical system; determining whether a distance between the position of the target portion of the object and an irradiation region of the positioning lamp is less than a distance threshold; and controlling, in response to determining that the distance between the position of the target portion of the object and the irradiation region of the positioning lamp is less than the distance threshold, the positioning lamp of the medical system to be turned off.

In some embodiments, the medical system may further include a radiation device, a projection device, and at least one processor in communication with the radiation device and the projection device. The radiation device may be configured to perform a medical procedure on the object by emitting radiation beams toward the object. The projection device may be configured to project reference image data associated with the object to a target position. The reference image data may provide guidance information associated with the medical procedure for the object. The at least one processor may be configured to control at least one of the radiation device or the projection device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
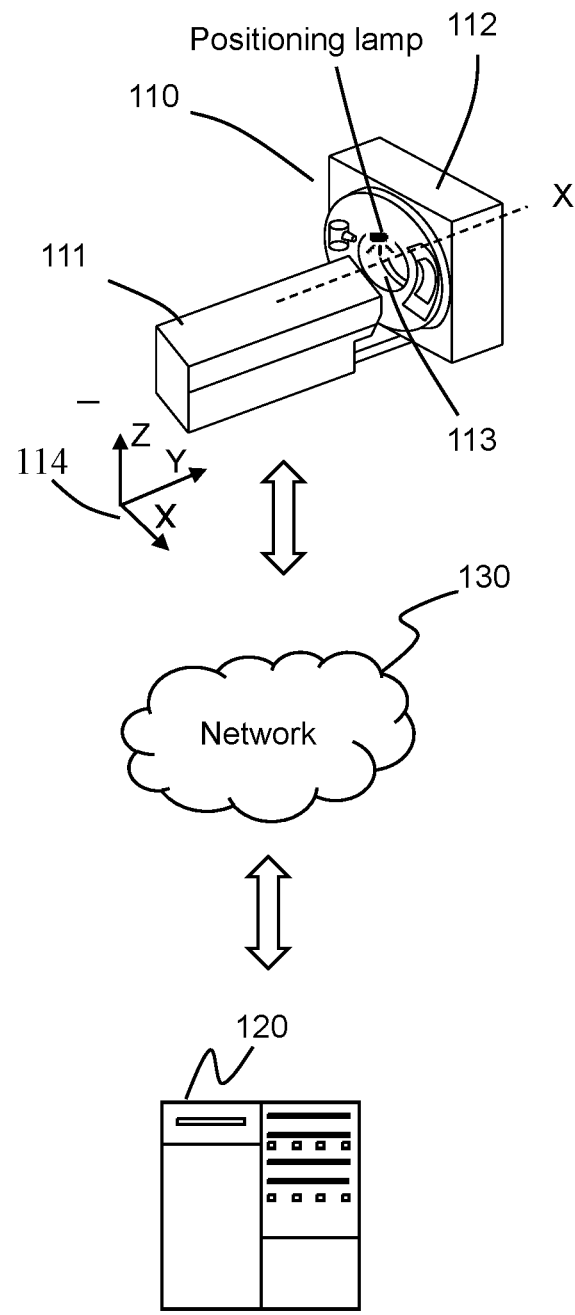
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block," as used herein, refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and methods for non-invasive biomedical imaging/treatment, such as for disease diagnostic, disease therapy, or research purposes. In some embodiments, the systems may include an imaging system. The imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. In some embodiments, the systems may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc. It should be noted that the medical system described below is merely provided for illustration purposes, and not intended to limit the scope of the present disclosure.

Conventionally, in practical applications, before an object (e.g., a patient or a portion thereof) is performed a medical procedure (e.g., observation, treatment), the object needs to be placed on a table of the medical system (e.g., a CT system) in the required posture (which may be referred to as "first positioning phase" for illustration purposes in the present disclosure). After the first positioning phase is completed, with the assistance of a positioning lamp (e.g., a laser lamp) of the medical system, a user (e.g., a doctor, a radiologist, a nurse) may move the object to a desired position in a detection region of the medical system for performing the medical procedure (which may be referred to as "second positioning phase" for illustration purposes in the present disclosure). The first positioning phase and the second positioning phase may be collectively referred to as a positioning phase. As used herein, the "positioning phase" may refer to operations (or process) of allowing the object to maintain a certain position and posture on the table of the medical system and determining a desired position of the object for performing the medical procedure.

During the second positioning phase, an operation (e.g., turning on, turning off) of the positioning lamp of the medical system needs to be manually controlled by the user (e.g., a doctor, a radiologist, a nurse) to help the user move the object to the desired position, which is inefficient and cumbersome to operate. To address the above-mentioned problems, an aspect of the present disclosure provides a medical system. The system may determine a working stage of the medical system and a position of a target portion of the object in the medical system. According to the working stage of the medical system and the position of the target portion of the object in the medical system, the system may automatically control the operation of the positioning lamp of the medical system, which realizes the automatic control of the positioning lamp, improves the operation efficiency, and simplifies the operation complexity.

In addition, the first positioning phase may be completed with the assistance of the user (e.g., the doctor, the radiologist, the nurse) to helf the positioning of the object. Therefore, during the first positioning phase, the user needs to enter and stay in a shielded room of the medical system, which makes the user suffers unnecessary radiation. After the first positioning phase is completed, the user leaves the shielded room and enters a control room of the medical system to operate the medical system to complete the medical procedure, which makes the user needs to walk back and forth between the shielded room and the control room, thereby reducing work efficiency. To address the above-mentioned problems, in some embodiments of the present disclosure, the medical system may include a radiation device and a projection device. The radiation device may be configured to perform the medical procedure on the object by emitting radiation beams toward the object. The projection device may be configured to project reference image data associated with the object to a target position. The reference image data may provide guidance information associated with the medical procedure for the object. According to the embodiments of the present disclosure, the object may complete the first positioning phase by himself (or herself) according to the reference image data projected by the projection device, thereby avoiding, in the first positioning phase, the user from entering the shielded room, reducing unnecessary radiation suffered by the user, and improving work efficiency.

FIG. 1 is a schematic diagram illustrating an exemplary medical system according to some embodiments of the present disclosure. As illustrated, the medical system 100 may include a radiation device 110, a processing device 120, and a network 130. The components of the medical system 100 may be connected in one or more of various ways. Mere by way of example, as illustrated in FIG. 1, the radiation device 110 may be connected to the processing device 120 through the network 130. As another example, the radiation device 110 may be connected to the processing device 120 directly.

The radiation device 110 may be configured to perform a medical procedure on an object (or a portion thereof) by emitting radiation beams (e.g., x-ray, gamma-ray) toward the object (or the portion thereof). In the present disclosure, the object may include a biological object and/or a non-biological object. The biological object may be a human being, an animal, a plant, or a specific portion, organ, and/or tissue thereof. For example, the object may include a head, a neck, a thorax, a heart, a stomach, a blood vessel, a soft tissue, a tumor, a nodule, or the like, or any combination thereof. In some embodiments, the object may be a man-made composition of organic and/or inorganic matters that are with or without life.

In the present disclosure, a representation of an object (e.g., a patient, a subject, or a portion thereof) in an image may be referred to as "object" for brevity. For instance, a representation of an organ or tissue (e.g., a heart, a liver, a lung) in an image may be referred to as an organ or tissue for brevity. Further, an image including a representation of an object may be referred to as an image of an object or an image including an object for brevity. Still further, an operation performed on a representation of an object in an image may be referred to as an operation performed on an object for brevity. For instance, a segmentation of a portion of an image including a representation of an organ or tissue from the image may be referred to as segmentation of an organ or tissue for brevity.

In some embodiments, the radiation device 110 may be or include an imaging device. The imaging device may be configured to acquire imaging data relating to the object. For example, the imaging device may scan the object or a portion thereof that is located within its detection region and generate imaging data relating to the object or the portion thereof. The imaging data relating to the object may include an image, projection data, or a combination thereof. In some embodiments, the imaging data may include two-dimensional (2D) imaging data (e.g., a slice image), three-dimensional (3D) imaging data, four-dimensional (4D) imaging data (a series of 3D images over time), or the like, or any combination thereof. In some embodiments, the imaging device may include a single modality imaging device. For example, the imaging device may include a digital subtraction angiography (DSA), a positron emission tomography (PET) device, a single-photon emission computed tomography (SPECT) device, a magnetic resonance imaging (MRI) device (also referred to as an MR device, an MR scanner), a computed tomography (CT) device, an ultrasonography scanner, a digital radiography (DR) scanner, a digital radiography (DR) device, or the like, or any combination thereof. In some embodiments, the imaging device may include a multi-modality imaging device. Exemplary multi-modality imaging devices may include a PET-CT device, a PET-MR device, or the like, or a combination thereof.

In some embodiments, the radiation device 110 may be or include a treatment device (e.g., an RT device). The treatment device may be configured to deliver a radiotherapy treatment to the object. For example, the treatment device may deliver one or more radiation beams to a treatment region (e.g., a tumor) of an object for causing an alleviation of the object's symptom. In some embodiments, the treatment device may include a conformal radiation therapy device, an image-guided radiation therapy (IGRT) device, an intensity-modulated radiation therapy (IMRT) device, an intensity-modulated arc therapy (IMAT) device, an emission guided radiation therapy (EGRT), or the like, or a combination thereof.

The processing device 120 may control the radiation device 110 and process data and/or information obtained from the radiation device 110. For example, the processing device 120 may determine a working stage of the medical system 100 and a position of a target portion of an object in the medical system 100. Further, the processing device 120 may control an operation of a positioning lamp of the medical system 100 based on the working stage of the medical system 100 and the position of the target portion of the object in the medical system 100. In some embodiments, the processing device 120 may include a central processing unit (CPU), a digital signal processor (DSP), a system on a chip (SoC), a microcontroller unit (MCU), or the like, or any combination thereof. In some embodiments, the processing device 120 may include a mobile device, a computer (e.g., a tablet computer, a laptop computer), a wearable device, a user console, a single server, or a server group, etc. The server group may be centralized or distributed. In some embodiments, the processing device 120 may be local or remote. For example, the processing device 120 may access information and/or data stored in the radiation device 110 via the network 130. As another example, the processing device 120 may be directly connected to the radiation device 110 to access stored information and/or data. In some embodiments, the processing device 120 may be implemented on a cloud platform. In some embodiments, the processing device 120 or a portion of the processing device 120 may be integrated into the radiation device 110. In some embodiments, the processing device 120 may be implemented by a computing device 200 including one or more components as described in FIG. 2.

The network 130 may include any suitable network that can facilitate the exchange of information and/or data for the medical system 100. In some embodiments, one or more components (e.g., the radiation device 110, the processing device 120) of the medical system 100 may communicate information and/or data with one or more other components of the medical system 100 via the network 130. For example, the processing device 120 may obtain data from the radiation device 110 via the network 130. In some embodiments, one or more components (e.g., the radiation device 110, the processing device 120) of the medical system 100 may communicate information and/or data with one or more external resources such as an external database of a third party, etc.

For illustration purposes, the following descriptions are provided regarding a CT device as the radiation device 110 unless otherwise stated. It should be noted that the descriptions of the CT device in the present disclosure are merely provided for illustration, and not intended to limit the scope of the present disclosure.

For example, as shown in FIG. 1, the radiation device 110 may be a CT device. In some embodiments, the radiation device 110 may include a table 111 and a gantry 112. The object may be positioned on the table 111. In some embodiments, the table 111 may be movable along a long axis X of a cavity 113 formed by the gantry 112. In some embodiments, the table 111 may be configured to rotate and/or translate along different directions to move the object to a desired position (e.g., an imaging position of the CT device for imaging) in the cavity 113. In some embodiments, one side of the gantry 112 may be provided with a radiation source (also referred to as a ball tube); the other side of the gantry 112 opposite to the radiation source may be provided with a detector. The radiation source may emit radioactive rays to the object. The detector may detect radiation events (e.g., x-ray photons, gamma-ray photons) emitted from an imaging region of the CT device. In some embodiments, a user (e.g., the doctor, the radiologist, a nurse) may operate the processing device 120 (also referred to as a console) to control the CT device. For example, the user may operate the processing device 120 to control the radiation source and the detector. In some embodiments, the processing device 120 may receive data collected by the detector and process the data to reconstruct a CT image.

For illustration purposes, a coordinate system 114 is provided in FIG. 1. The coordinate system 114 may be a Cartesian system including an X-axis, the Y-axis, and a Z-axis. The X-axis and the Y-axis shown in FIG. 1 may be horizontal, and the Z-axis may be vertical. As illustrated, the positive X direction along the X-axis may be from the left side to the right side of the table 111 viewed from the direction facing the front of the radiation device 110; the positive Y direction along the Y-axis shown in FIG. 1 may be from the end to the head of the table 111; the positive Z direction along the Z-axis shown in FIG. 1 may be from the lower part to the upper part of the radiation device 110.

It should be noted that the above description of the medical system 100 is merely provided for the purposes of illustration, and not intended to limit the scope of the present disclosure. For persons having ordinary skills in the art, multiple variations and modifications may be made under the teachings of the present disclosure. For example, the medical system 100 may include one or more additional components (e.g., a storage device) and/or one or more components of the medical system 100 described above may be omitted. Additionally or alternatively, two or more components of the medical system 100 may be integrated into a single component. A component of the medical system 100 may be implemented on two or more sub-components.

Figure 2:
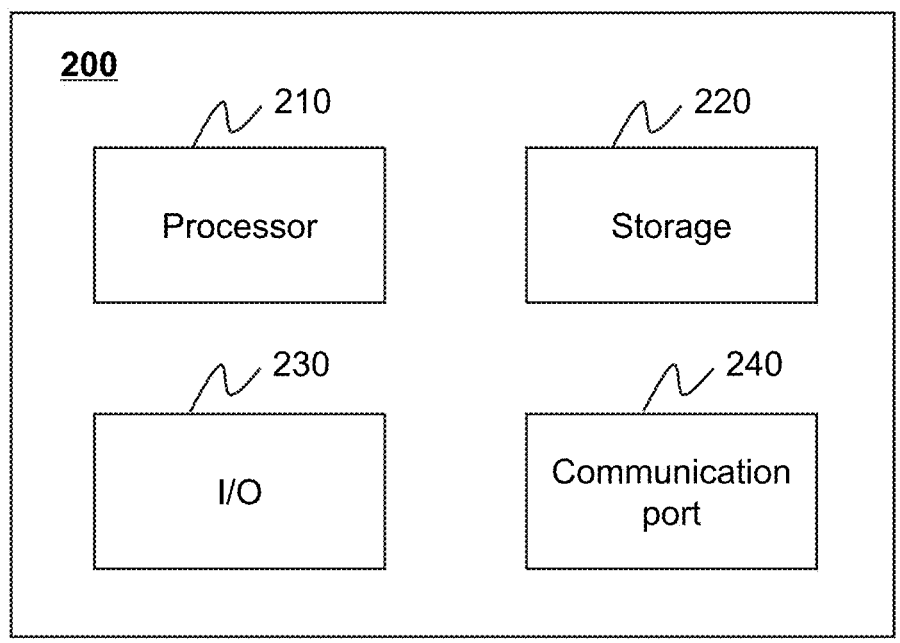
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. The computing device 200 may be used to implement any component of the medical system 100 as described herein. For example, the processing device 120 may be implemented on the computing device 200, via its hardware, software program, firmware, or a combination thereof. Although only one such computing device is shown, for convenience, the computer functions relating to the medical system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, objects, components, data structures, procedures, modules, and functions, which perform particular functions described herein. For example, the processor 210 may determine a working stage of the medical system 100 and a position of a target portion of an object in the medical system 100. Further, the processor 210 may control an operation of a positioning lamp of the medical system 100 based on the working stage of the medical system 100 and the position of the target portion of the object in the medical system 100. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or a combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from or generated by any component of the medical system 100. In some embodiments, the storage 220 may store data and/or instructions that the processor 210 may execute or use to perform exemplary methods described in the present disclosure. For example, the storage 220 may store a program for the processor 210 to execute to control the operation of the positioning lamp of the medical system 100. In some embodiments, the storage 220 may include a mass storage device, a removable storage device, a volatile read-and-write memory, a read-only memory (ROM), or the like, or a combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc.

The I/O 230 may input and/or output signals, data, information, etc. In some embodiments, the I/O 230 may enable a user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 130) to facilitate data communications. The communication port 240 may establish connections between the processing device 120 and one or more components (e.g., the radiation device 110) of the medical system 100. The connection may be a wired connection, a wireless connection, any other communication connection that can enable data transmission and/or reception, and/or a combination of these connections.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or terminal device. A computer may also act as a server if appropriately programmed.

Figure 3:
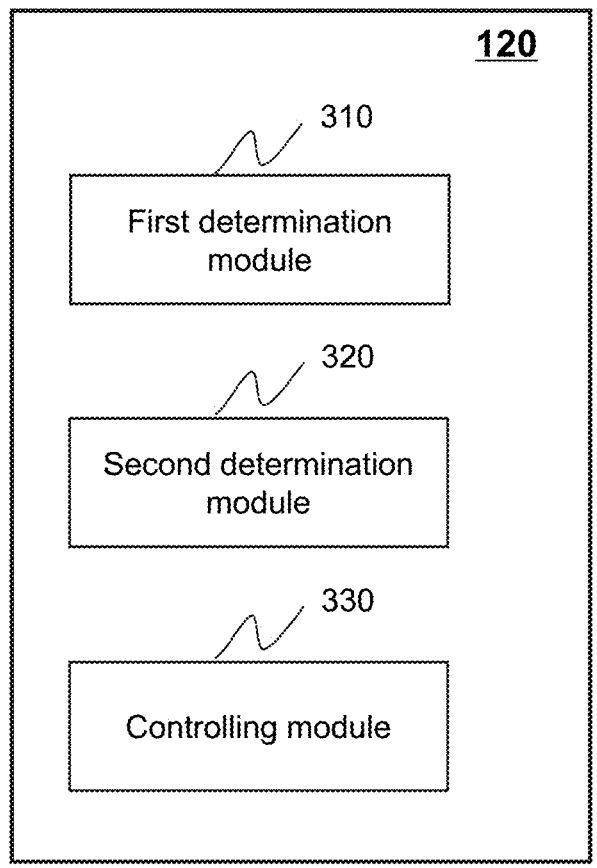
FIG. 3 is a block diagram illustrating an exemplary processing device according to some embodiments of the present disclosure.

FIG. 3 is a block diagram illustrating an exemplary processing device according to some embodiments of the present disclosure. The processing device 120 may be implemented on the computing device 200 (e.g., the processor 210) illustrated in FIG. 2. The processing device 120 may include a first determination module 410, a second determination module 420, and a controlling module 430.

The first determination module 410 may be configured to determine a working phase of the medical system (e.g., the medical system 100). In some embodiments, the first determination module 410 may obtain workflow information of the medical system in a current medical procedure of an object. Further, the first determination module 410 may determine the working phase of the medical system based on the workflow information of the medical system in the current medical procedure of the object. More descriptions regarding the determining of the working phase of the medical system may be found elsewhere in the present disclosure, for example, operation 410 in FIG. 4 and relevant descriptions thereof.

The second determination module 420 may be configured to determine a position of a target portion of an object in the medical system based on one or more images associated with the object captured by an imaging sensor. In some embodiments, the second determination module 420 may identify the target portion of the object from the one or more images associated with the object. Further, the second determination module 420 may obtain a position of the target portion of the object in a first coordinate system of the imaging sensor or the one or more images. According to the position of the target portion of the object in the first coordinate system of the imaging sensor or the one or more images, the second determination module 420 may determine the position of the target portion of the object in a second coordinate system (e.g., the coordinate system 114 illustrated in FIG. 1) of the medical system. More descriptions regarding the determining of the position of the target portion of the object in the medical system may be found elsewhere in the present disclosure, for example, operation 420 in FIG. 4 and relevant descriptions thereof.

The controlling module 430 may be configured to control an operation of a positioning lamp of the medical system based on the working phase of the medical system and the position of the target portion of the object in the medical system. In some embodiments, the controlling module 430 may determine whether the working phase of the medical system is the positioning phase. In response to determining that the working phase of the medical system is the positioning phase, the controlling module 430 may control the operation of the positioning lamp of the medical system based on an irradiation region of the positioning lamp and the position of the target portion of the object in the medical system. In response to determining that the working phase of the medical system is not the positioning phase, the controlling module 430 may control the positioning lamp of the medical system to keep turned off. More descriptions regarding the controlling of the operation of the positioning lamp may be found elsewhere in the present disclosure, for example, operation 430 in FIG. 4, FIG. 5, and relevant descriptions thereof.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, two or more of the modules may be combined into a single module, and any one of the modules may be divided into two or more units. For example, the first determination module 410 and the second determination module 420 may be combined as a single module which may both determine the working stage of the medical system and the position of the target portion of the object in the medical system. In some embodiments, the processing device 120 may include one or more additional modules. For example, the processing device 120 may also include a transmission module (not shown) configured to transmit signals (e.g., electrical signals, electromagnetic signals) to one or more components (e.g., the radiation device 110) of the medical system 100. As another example, the processing device 120 may include a storage module (not shown) used to store information and/or data (e.g., the working stage of the medical system, the one or more images associated with the object captured by the imaging sensor, the workflow information of the medical system, etc.) associated with the controlling of the medical system.

Figure 4:
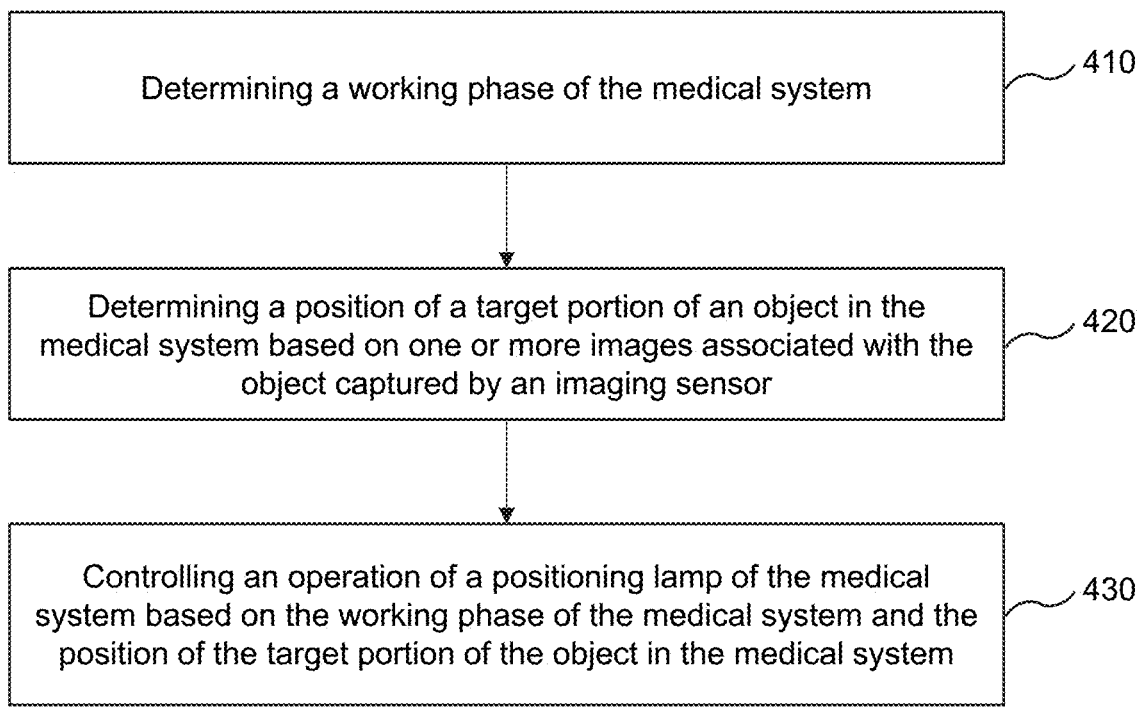
FIG. 4 is a flowchart illustrating an exemplary process for controlling a medical system according to some embodiments of the present disclosure.

FIG. 4 is a flowchart illustrating an exemplary process for controlling a medical system according to some embodiments of the present disclosure. In some embodiments, process 400 may be executed by the medical system 100. For example, the process 400 may be implemented as a set of instructions (e.g., an application) stored in a storage device (e.g., the storage 220). In some embodiments, the processing device 120 (e.g., the processor 210 of the computing device 200 and/or one or more modules illustrated in FIG. 3) may execute the set of instructions and may accordingly be directed to perform the process 400. The operations of the illustrated process presented below are intended to be illustrative. In some embodiments, the process 400 may be accomplished with one or more additional operations not described and/or without one or more of the operations discussed. Additionally, the order of the operations of process 400 illustrated in FIG. 4 and described below is not intended to be limiting.

In 410, the processing device 120 (e.g., the first determination module 410) (e.g., the processing circuits of the processor 210) may determine a working phase of the medical system (e.g., the medical system 100).

In some embodiments, a whole workflow of the medical system may be divided into a plurality of phases. Each of the plurality of phases may be a working phase of the medical system. Merely by way of example, the working phase of the medical system may include a positioning phase, a scanning phase, and/or a scanning completion phase. As disclosed elsewhere in the present disclosure, the "positioning phase" may refer to operations (or process) of allowing the object to maintain a certain position and posture on the table of the medical system and determining a desired position of the object for performing the medical procedure. As used herein, the medical procedure may refer to a series of actions that help the object treat diseases (e.g., disease observation, disease treatment). The scanning phase may refer to a phase in which the medical system performs the medical procedure. The scanning completion phase may refer to a phase after the completion of performing the medical procedure, for example, from the completion of performing the medical procedure to the beginning of a next workflow of the medical system. Taking a CT system as an example, when an object is scanned for imaging using the CT system, in a positioning phase of the CT system, the object may be placed on a table (e.g., the table 111 illustrated in FIG. 1), and then the table that carries the object may be controlled by the processing device 120 to move along a long axis of a cavity (e.g., the cavity 113 illustrated in FIG. 1) of the CT system to a desired position for imaging in the cavity. Then, in a scanning phase of the CT system, the processing device 120 may control a gantry (e.g., the gantry 112 illustrated in FIG. 1) of the CT system to rotate at high speed, the radiation source to emit radioactive rays to the object, and the detector to detect X-rays passing through the object to form data. Further, in a scanning completion phase of the CT system, the object may be exited from the CT system and the processing device 120 may receive the data from the detector and process the data to reconstruct a CT image of the object.

In some embodiments, the processing device 120 may obtain workflow information of the medical system in a current medical procedure of an object. The workflow information of the medical system may refer to information recorded by the medical system in real time during a whole workflow of the medical system. Still taking the CT system as an example, the workflow information of the CT system may include object data entry, object placement and protection, scanning program selection, scanning, scanning completion, etc. The object data entry may include inputting object's data to the processing device 120 manually or through an operating system (e.g., a picture archiving and communication system, PACS) or application of the processing device 120. The object placement and protection may include placing the object on the table of the CT system in a required posture according to the inspection purpose on a checklist of the object; raising the table to a proper height; moving the table that carries the object to the cavity of the CT system to make a scanned part (also referred to as a target part) of the object in a desired position (e.g., a center of the cavity) in the cavity; and protecting the unscanned parts of the object. The scanning program selection may include selecting an appropriate scan sequence from preset scan sequences according to the inspection purpose on a checklist of the object.

Further, the processing device 120 may determine the working phase of the medical system based on the workflow information of the medical system in the current medical procedure of the object. The workflow information of the medical system may correspond to the working phases of the medical system. For example, the object placement and protection may correspond to the positioning phase; the scanning program selection and scanning may correspond to the scanning phase; the scanning completion may correspond to the scanning completion phase. The processing device 120 may determine the working phase of the medical system based on the correspondence between the workflow information and the working phases. For example, when the workflow information of the medical system in the current medical procedure of the object is the object placement and protection, the processing device 120 may determine that the working phase of the medical system is the positioning phase. In some embodiments, during the operation of the medical system (e.g., the CT system), the workflow information and network protocols corresponding to the workflow information may be generated. The processing device 120 may obtain the network protocols corresponding to the workflow information and determine the working phase of the medical system based on the network protocols corresponding to the workflow information. For example, the processing device 120 may obtain a current network protocol that is running and determine the workflow information based on the current network protocol. Further, the processing device 120 may determine the working phase of the medical system based on the correspondence between the workflow information and the working phases.

In some embodiments, in a working phase of the medical system, a user (e.g., the doctor, the radiologist, a nurse) of the medical system needs to enter relevant information of the working phase into the imaging system. During the process of entering the relevant information, the medical system may perform operations such as confirming/loading a network protocol. The processing device 120 may determine the working phase of the medical system by obtaining the most recently running network protocol.

In 420, the processing device 120 (e.g., the second determination module 420) (e.g., the processing circuits of the processor 210) may determine a position of a target portion of an object in the medical system based on one or more images associated with the object captured by an imaging sensor.

In some embodiments, the imaging sensor may include a visible light imaging sensor, an infrared imaging sensor, etc. For example, the visible light imaging sensor may include a camera, a video recorder, etc. The camera may include a gun camera, a dome camera, an integrated camera, a monocular camera, a binocular camera, a multi-view camera, or the like, or any combination thereof. The video recorder may include a PC digital video recorder (DVR), an embedded DVR, or the like, or any combination thereof. As another example, the visible light imaging sensor may include an infrared thermal imager. In some embodiments, the imaging sensor may be arranged on a radiation device (e.g., the radiation device 100) or above the radiation device. For example, the imaging sensor may be arranged at the table of the radiation device or the gantry of the radiation device. In some embodiments, the imaging sensor may be turned on synchronously with the radiation device or when the working phase of the medical system is the positioning phase.

In some embodiments, the processing device 120 may direct the imaging sensor to capture the one or more images associated with the object and obtain the one or more images accordingly. In some embodiments, the processing device 120 may obtain or determine the one or more images from a video associated with the object captured by the imaging sensor.

In some embodiments, the target portion of the object may refer to a part of the object sensitive to a light emitted by a positioning lamp (e.g., a laser lamp) of the medical system. Merely by way of example, the target portion of the object may be eyes. In some embodiments, the processing device 120 may identify the target portion of the object from the one or more images associated with the object. For example, the processing device 120 may identify the target portion of the object from the one or more images associated with the object using a trained neural network model. Specifically, the processing device 120 may input the one or more images associated with the object into the trained neural network model and determine the target portion of the object based on an output of the trained neural network model. The processing device 120 may obtain the trained neural network model based on a plurality of training samples. Specifically, the processing device 120 may input the plurality of training samples into a preliminary neural network model and update the parameters of the preliminary neural network model based on the plurality of training samples to obtain the trained neural network model. In some embodiments, the processing device 120 may obtain a plurality of images associated with different or same object. The target portion of the object in each of the plurality of images may be marked manually. The plurality of marked images may be used as the plurality of training samples.

Further, the processing device 120 may obtain a position of the target portion of the object in a first coordinate system of the imaging sensor or the one or more images. The first coordinate system may be a camera coordinate system of the imaging sensor. According to the position of the target portion of the object in the first coordinate system of the imaging sensor or the one or more images, the processing device 120 may determine the position of the target portion of the object in a second coordinate system (e.g., the coordinate system 114 illustrated in FIG. 1) of the medical system. More descriptions of the second coordinate system may be found elsewhere in the present disclosure (e.g., FIG. 1 and the description thereof). The processing device 120 may determine the position of the target portion of the object in the second coordinate system of the medical system by performing a coordinate conversion on the position of the target portion of the object in the first coordinate system based on a preset algorithm. The preset algorithm may be default settings of the medical system 100 or may be adjustable under different situations. In the present disclosure, the position of the target portion may include coordinate information of the target portion and information (e.g., a size, a boundary, coordinates of points in the region) of a region where the target portion is located.

In 430, the processing device 120 (e.g., the controlling module 430) (e.g., the processing circuits of the processor 210) may control an operation of a positioning lamp of the medical system based on the working phase of the medical system and the position of the target portion of the object in the medical system.

In some embodiments, the positioning lamp of the medical system may be a laser lamp. The positioning lamp may be arranged on the radiation device (e.g., the radiation device 100). For example, the positioning lamp may be arranged on the gantry of the radiation device. As another example, the positioning lamp may be arranged inside of the cavity formed by the gantry. In some embodiments, the controlling the operation of the positioning lamp may include controlling the positioning lamp to be turned on, turned off, to keep turned on, and/or turned off.

In some embodiments, the processing device 120 may determine whether the working phase of the medical system is the positioning phase. In response to determining that the working phase of the medical system is the positioning phase, the processing device 120 may control the operation of the positioning lamp of the medical system based on an irradiation region of the positioning lamp and the position of the target portion of the object in the medical system. In response to determining that the working phase of the medical system is not the positioning phase, the processing device 120 may control the positioning lamp of the medical system to keep turned off. More descriptions of the controlling of the operation of the positioning lamp may be found elsewhere in the present disclosure (e.g., FIG. 5 and the description thereof).

It should be noted that the above description regarding the process 400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 400 may be accomplished with one or more additional operations not described and/or without one or more of the operations discussed above. For example, the process 400 may include an additional transmitting operation in which the processing device 120 may transmit signals (e.g., a control signal) to the positioning lamp of the radiation device 110 to implement the controlling of the positioning lamp. As another example, the process 400 may include an additional storing operation in which the processing device 120 may store information and/or data (e.g., the working stage of the medical system, the one or more images associated with the object captured by the imaging sensor, the workflow information of the medical system, etc.) associated with the controlling of the medical system in a storage device (e.g., the storage 220) disclosed elsewhere in the present disclosure.

Figure 5:
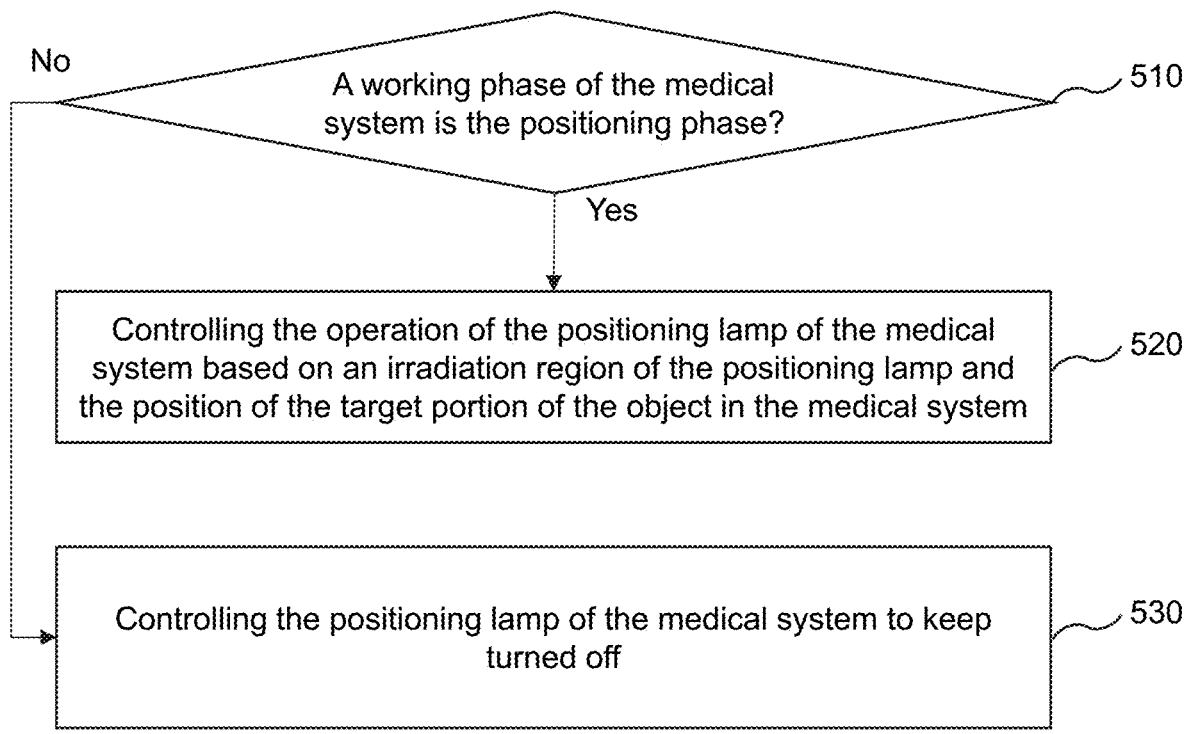
FIG. 5 is a flowchart illustrating an exemplary process for controlling a medical system according to some embodiments of the present disclosure.

FIG. 5 is a flowchart illustrating an exemplary process for controlling a medical system according to some embodiments of the present disclosure. In some embodiments, process 500 may be executed by the medical system 100. For example, the process 500 may be implemented as a set of instructions (e.g., an application) stored in a storage device (e.g., the storage 220). In some embodiments, the processing device 120 (e.g., the processor 210 of the computing device 200 and/or one or more modules illustrated in FIG. 3) may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting. Operation 430 may be performed according to process 500 as described in FIG. 5.

In 510, the processing device 120 (e.g., the controlling module 430) (e.g., the processing circuits of the processor 210) may determine whether a working phase of a medical system (e.g., the medical system 100) is a positioning phase.

The processing device 120 may obtain the one or more images associated with the object and determine whether the working phase of the a medical system (e.g., the medical system 100) is the positioning phase based on the one or more images associated with the object. As described in connection with FIG. 4, the processing device 120 may direct an imaging sensor to capture the one or more images associated with the object and obtain the one or more images accordingly or obtain (or determine) the one or more images from a video associated with the object captured by the imaging sensor.

In some embodiments, the one or more images may include one or more first images of the object and/or one or more second images of the object and a target object. A first image may refer to an image that includes the object. A second image may refer to an image that includes both the object and the target object. In some embodiments, the target object may be an operator of the medical system (e.g., the doctor, the radiologist, a nurse) of the medical system. In some embodiments, the one or more first images and the one or more second images may be captured by a same imaging sensor. The one or more first images and the one or more second images may be separated manually or using a model. For example, the processing device 120 may determine whether a target object is included in each of the one or more images using a model. If the target object is included in an image, the processing device 120 may designate the image as a second image. If the target object is not included in an image, the processing device 120 may designate the image as a first image. In some alternative embodiments, the one or more first images and the one or more second images may be captured by different imaging sensors. For example, the imaging sensors may include a first imaging sensor arranged near a table (e.g., the table 111) of the medical system and a second imaging sensor arranged above a radiation device (e.g., the radiation device 110) of the medical system (e.g., on a ceiling above the radiation device). The first imaging sensor may be configured to capture the one or more first images. The second imaging sensor may be configured to capture the one or more second images.

According to the one or more first images of the object and/or the one or more second images, the processing device 120 may determine whether the object is located on the table of the medical system. In some embodiments, the processing device 120 may determine whether the one or more first images of the object and/or the one or more second images include a table. If the one or more first images of the object and/or the one or more second images does not include the table, the processing device 120 may determine that the object is not located on the table of the medical system. In some embodiments, the processing device 120 may determine whether the object is located on the table of the medical system using a trained first model (e.g., a neural network model). Specifically, the processing device 120 may input the one or more first images and/or the one or more second images into the trained first model and determine whether the object is located on the table of the medical system based on an output of the trained first model. In some embodiments, the output of the trained first model may include a determination result of whether the object is located on the table of the medical system. The determination result may include that the object is located on the table of the medical system or the object is not located on the table of the medical system. In some embodiments, the output of the trained first model may include a distance between the object and the table of the medical system. The processing device 120 may determine whether the object is located on the table of the medical system based on the distance between the object and the table of the medical system. For example, when the distance between the object and the table of the medical system is less than or equal to a distance threshold (also referred to as first distance threshold), the processing device 120 may determine that the object is located on the table of the medical system; when the distance between the object and the table of the medical system is larger than the first distance threshold, the processing device 120 may determine that the object is not located on the table of the medical system. The first distance threshold may be default settings of the medical system 100 or may be adjustable under different situations. In some embodiments, the processing device 120 may obtain the trained first model based on a plurality of training samples. Specifically, the processing device 120 may input the plurality of training samples into a preliminary first model and update the parameters of the preliminary first model based on the plurality of training samples to obtain the trained first model. In some embodiments, each of at least a portion of the plurality of training samples may be an image that includes an object and a table. In some embodiments, each of at least a portion of the plurality of training samples may be an image that includes an object and does not include a table.

In response to determining that the object is located on the table, the processing device 120 may determine whether a distance between the table and the target object is less than or equal to a distance threshold (also referred to as second distance threshold) based on the one or more second images. The distance threshold may be default settings of the medical system 100 or may be adjustable under different situations. In some embodiments, the processing device 120 may determine distance between the table and the target object using a trained second model (e.g., a neural network model). Specifically, the processing device 120 may input the one or more second images into the trained second model and determine the distance between the table and the target object based on an output of the trained second model. In some embodiments, the processing device 120 may obtain the trained second model based on a plurality of training samples. Specifically, the processing device 120 may input the plurality of training samples into a preliminary second model and update the parameters of the preliminary second model based on the plurality of training samples to obtain the trained second model. In some embodiments, each of at least a portion of the plurality of training samples may be an image that includes a target object and a table.

Further, the processing device 120 may determine whether the distance between the table and the target object is less than or equal to the second distance threshold. In response to determining that the distance between the table and the target object is less than or equal to the second distance threshold, the processing device 120 may determine that the working phase of the medical system is the positioning phase. In response to determining that the distance between the table and the target object is larger than the second distance threshold, the processing device 120 may determine that the working phase of the medical system is not the positioning phase.

In some alternative embodiments, the processing device 120 may determine whether a distance between the target object and other component (e.g., the radiation device, a gantry of the radiation device) is less than or equal to a distance threshold (also referred to as third distance threshold) and determine whether the working phase of the medical system is the positioning phase based on a determination result of whether the distance between the target object and other component is less than or equal to the third distance threshold. For example, when the distance between the target object and other component is less than or equal to the third distance threshold, the processing device 120 may determine that the working phase of the medical system is the positioning phase; when the distance between the target object and other component is larger than the third distance threshold, the processing device 120 may determine that the working phase of the medical system is not the positioning phase.

In some embodiments, the processing device 120 may determine a duration of time that the distance between the table and the target object is less than or equal to the second distance threshold (or the distance between the target object and other component is less than or equal to the third distance threshold). Further, when the duration of time is larger than or equal to a preset value, the processing device 120 may determine that the working phase of the medical system is the positioning phase; when the length of time is less than the preset value, the processing device 120 may determine that the working phase of the medical system is not the positioning phase. The preset value may be default settings of the medical system 100 or may be adjustable under different situations.

In some embodiments, when the working phase of the medical system is the positioning phase, the processing device 120 may proceed to perform operation 520; when the working phase of the medical system is not the positioning phase, the processing device 120 may proceed to perform operation 530.

In 520, the processing device 120 (e.g., the controlling module 430) (e.g., the processing circuits of the processor 210) may control the operation of the positioning lamp of the medical system based on an irradiation region of the positioning lamp and the position of the target portion of the object in the medical system.

In some embodiments, the processing device 120 may control the positioning lamp of the medical system based on a position or a movement state of the table of the medical system. After the object is being placed on the table of the medical system in the required posture, the user (e.g., a doctor, a radiologist, a nurse) may move the object to a desired position in a detection region of the medical system by moving the table of the medical system. The user may start the movement of the table through an interface. The interface may include a button, a touch screen, a voice interaction, a brain-computer interface, etc. For example, when the interface includes the button, the user may send a moving instruction to the processing device 120 by pressing the button. As another example, when the interface includes the touch screen, the user may send the moving instruction to the processing device 120 by tapping or swiping the touch screen. As a further example, when the interface includes the voice interaction, the user may send the moving instruction to the processing device 120 by voice. As a still further example, when the interface includes the brain-computer interface, the user may send the moving instruction to the processing device 120 by an EEG (Electroencephalogram) acquisition device. The EEG acquisition device may collect and process an EEG signal of the user to obtain the moving instruction issued by the user. Further, the processing device 120 may start the movement of the table based on the received moving command. In some embodiments, the processing device 120 may turn on the positioning lamp of the medical system when starting the movement of the table. In some alternative embodiments, the processing device 120 may turn on the positioning lamp of the medical system when the table is moved to a preset position. For example, the processing device 120 may turn on the positioning lamp of the medical system when one third of the table enters a cavity (e.g., the cavity 113 illustrated in FIG. 1) of the medical system.

In some embodiments, the table 111 may be movable in a plurality of movement planes relative to the positioning lamp of the medical system. For each movement plane, the imaging sensor may acquire an real-time, non-invasive image of the table 111 surface with the object on the table 111 to show the table 111 surface and the exterior of the object. In some embodiments, the processing device 120 may control the positioning lamp of the medical system to be turned on when starting the movement of the table. Simultaneously, the processing device 120 may control the table that carries the object to move along a long axis (e.g., the long axis X illustrated in FIG. 1) of the cavity to enter the cavity. With the assistance of the positioning lamp of the medical system, the user may move the object to the desired position or adjust a position of the object in the detection region in the cavity of the medical system. The processing device 120 may determine a position of a target portion of the object in the medical system and whether a distance between the position of the target portion of the object and an irradiation region of the positioning lamp is less than a distance threshold (also referred to as a fourth distance threshold) before the target portion of the object is at the desired position. The fourth distance threshold may be default settings of the medical system 100 or may be adjustable under different situations. In some embodiments, the irradiation region of the positioning lamp may be in the cavity. In response to determining that the distance between the position of the target portion of the object and the irradiation region of the positioning lamp is less than the fourth distance threshold, the processing device 120 may control the positioning lamp of the medical system to be turned off.

In some embodiments, the processing device 120 may determine whether the position of the target portion of the object is within the irradiation region of the positioning lamp or determine whether the table 111 is movable in a movement plane the positioning lamp positioned in. In some embodiments, coordinates of the irradiation region of the positioning lamp may be measured in advance, transformed into the second coordinate system (e.g., the coordinate system 114 illustrated in FIG. 1) of the medical system, and stored in a storage device (e.g., the storage 220) of the medical system. In some embodiments, the processing device 120 may determine whether the position of the target portion of the object is within or at least partially overlaps with the irradiation region of the positioning lamp based on coordinates of the position of the target portion of the object and the coordinates of the irradiation region of the positioning lamp. If the position of the target portion of the object is not within or does not overlap with the irradiation region of the positioning lamp, the processing device 120 may determine that the position of the target portion of the object is not within the irradiation region of the positioning lamp. In response to determining that the position of the target portion of the object is not within the irradiation region of the positioning lamp, the processing device 120 may control the positioning lamp of the medical system to be/keep turned on. If the position of the target portion of the object is within or at least partially overlaps with the irradiation region of the positioning lamp, the processing device 120 may determine that the position of the target portion of the object is within the irradiation region of the positioning lamp. In response to determining that the position of the target portion of the object is within the irradiation region of the positioning lamp, the processing device 120 may control the positioning lamp of the medical system to be turned off, which may reduce or avoid the damage to the target portion (e.g., eyes) of the object caused by the light emitted by the positioning lamp.

In some embodiments, the processing device 120 may control the positioning lamp of the medical system to be turned off after the positioning lamp is turned on for a preset time. The preset time may be default settings of the medical system 100 or may be adjustable under different situations.

In 530, the processing device 120 (e.g., the controlling module 430) (e.g., the processing circuits of the processor 210) may control the positioning lamp of the medical system to be/keep turned off.

When the working phase of the medical system is not the positioning phase, the working phase of the medical system may be a scanning phase or a scanning completion phase. Therefore, the processing device 120 may control the positioning lamp of the medical system to keep turned off, which may reduce or avoid the energy loss of the positioning lamp and the damage to the object caused by the light emitted by the positioning lamp.

In the present disclosure, according to the working stage of the medical system, the position of the target portion of the object in the medical system, and/or the irradiation region of the positioning lamp, etc., the processing device 120 may automatically control the operation of the positioning lamp of the medical system, which realizes the automatic control of the positioning lamp, improves the operation efficiency, and simplifies the operation complexity.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
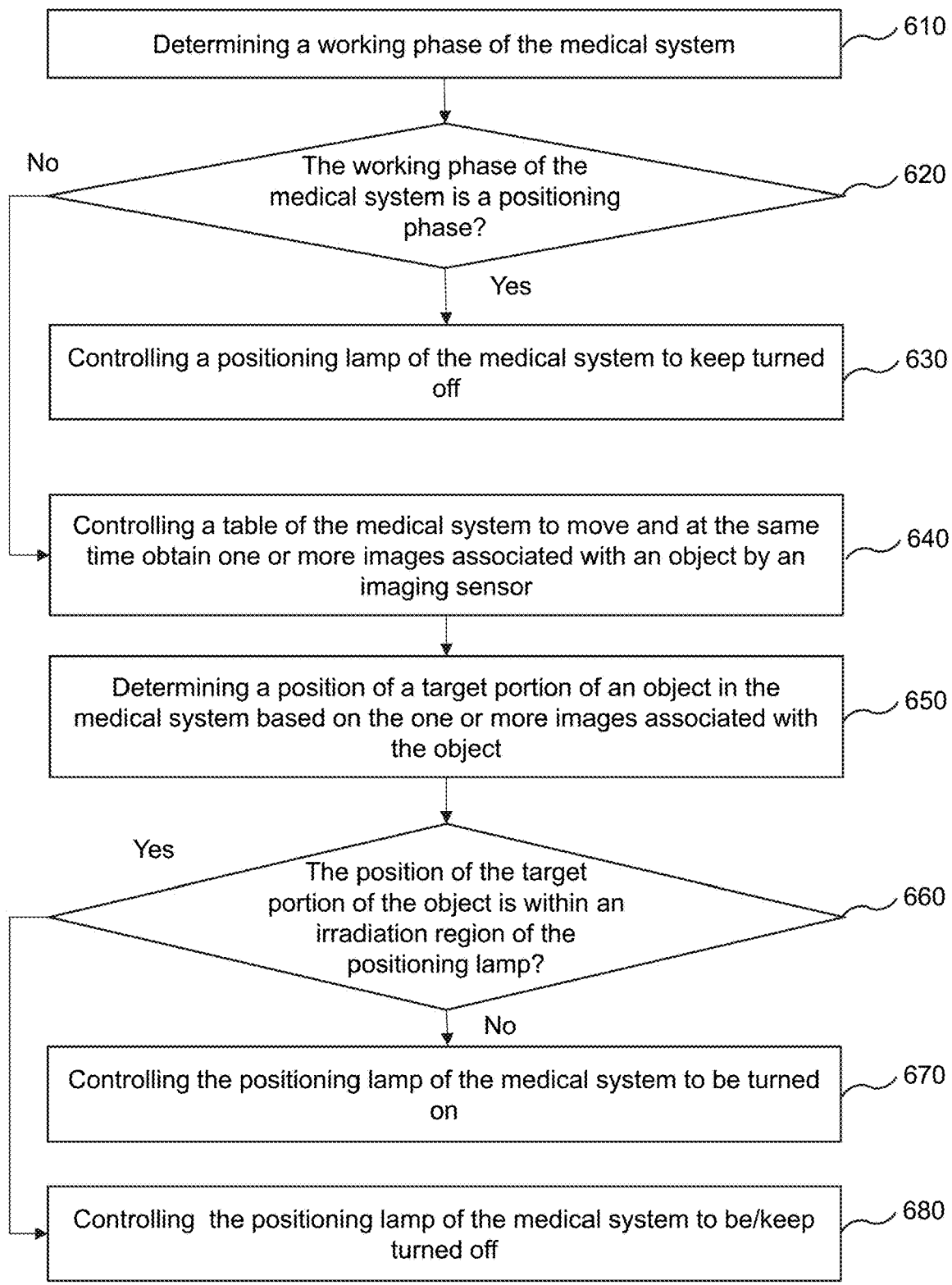
FIG. 6 is a flowchart illustrating an exemplary process for controlling a medical system according to some embodiments of the present disclosure.

FIG. 6 is a flowchart illustrating an exemplary process for controlling a medical system according to some embodiments of the present disclosure. In some embodiments, process 600 may be executed by the medical system 100. For example, the process 600 may be implemented as a set of instructions (e.g., an application) stored in a storage device (e.g., the storage 220). In some embodiments, the processing device 120 (e.g., the processor 210 of the computing device 200 and/or one or more modules illustrated in FIG. 3) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, the processing device 120 (e.g., the first determination module 410) (e.g., the processing circuits of the processor 210) may obtain a working phase of the medical system (e.g., the medical system 100). As described in connection with FIG. 5, the working phase of the medical system may include a positioning phase, a scanning phase, and/or a scanning completion phase. The working phase of the medical system may be obtained in a similar manner as operation 410 in FIG. 4, and relevant descriptions are not repeated here.

In 620, the processing device 120 (e.g., the controlling module 430) (e.g., the processing circuits of the processor 210) may determine whether the working phase of the medical system is the positioning phase. Whether the working phase of the medical system is the positioning phase may be determined in a similar manner as operation 510 in FIG. 5, and relevant descriptions are not repeated here. In some embodiments, in response to determining that the working phase of the medical system is not the positioning phase, the processing device 120 may proceed to perform operation 630. In response to determining that the working phase of the medical system is the positioning phase, the processing device 120 may proceed to perform operation 640.

In 630, the processing device 120 (e.g., the controlling module 430) (e.g., the processing circuits of the processor 210) may control a positioning lamp of the medical system to keep turned off.

In 640, the processing device 120 (e.g., the second determination module 420) (e.g., the processing circuits of the processor 210) may control a table (e.g., a table 111) of the medical system to move and at the same time obtain one or more images associated with an object by an imaging sensor. As described in connection with FIG. 4, the processing device 120 may direct the imaging sensor to capture the one or more images associated with the object and obtain the one or more images accordingly.

In 650, the processing device 120 (e.g., the second determination module 420) (e.g., the processing circuits of the processor 210) may determine a position of a target portion (e.g., eyes) of an object in the medical system based on the one or more images associated with the object. The position of the target portion of the object in the medical system may be determined in a similar manner as operation 420 in FIG. 4, and relevant descriptions are not repeated here.

In 660, the processing device 120 (e.g., the controlling module 430) (e.g., the processing circuits of the processor 210) may determine whether the position of the target portion of the object is within an irradiation region of the positioning lamp. Whether the position of the target portion of the object is within the irradiation region of the positioning lamp may be determined in a similar manner as operation 520 in FIG. 5, and relevant descriptions are not repeated here. In some embodiments, in response to determining that the position of the target portion of the object is not within the irradiation region of the positioning lamp, the processing device 120 may proceed to perform operation 670. In response to determining that the position of the target portion of the object is within the irradiation region of the positioning lamp, the processing device 120 may proceed to perform operation 680.

In 670, the processing device 120 (e.g., the controlling module 430) (e.g., the processing circuits of the processor 210) may control the positioning lamp of the medical system to be turned on. With the assistance of the positioning lamp of the medical system, a user (e.g., a doctor, a radiologist, a nurse) may move the object to a desired position or adjust a position of the object in the detection region in the cavity of the medical system, and then a medical procedure (e.g., observation, treatment) may be performed on the object.

In 680, the processing device 120 (e.g., the controlling module 430) (e.g., the processing circuits of the processor 210) may control the positioning lamp of the medical system to be/keep turned off, which may reduce or avoid the damage to the target portion (e.g., eyes) of the object caused by the light emitted by the positioning lamp.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 7:
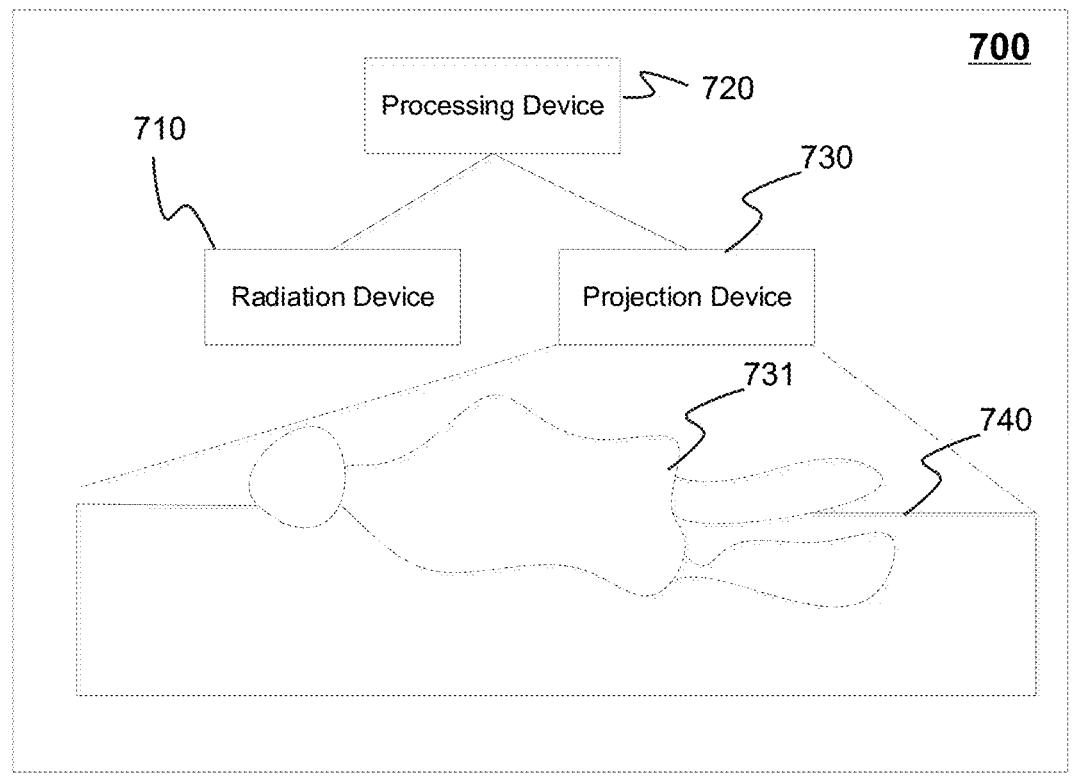
FIG. 7 is a schematic diagram illustrating an exemplary medical system according to some embodiments of the present disclosure.

FIG. 7 is a schematic diagram illustrating an exemplary medical system according to some embodiments of the present disclosure. As illustrated in FIG. 7, the medical system 700 may include a radiation device 710, a processing device 720, and a projection device 730.

The radiation device 710 may be configured to perform a medical procedure (e.g., observation, treatment) on an object by emitting radiation beams toward the object. As described in connection with FIG. 5, the radiation device 710 may be or include an imaging device (e.g., a DSA, a PET device, a SPECT device, an MRI device, a CT device, an ultrasonography scanner, a DR scanner, a DR device, etc.) or a treatment device (e.g., an RT device, a conformal radiation therapy device, an IGRT device, an IMRT device, an IMAT device, an EGRT, etc.). For example, the radiation device 710 may be a CT device. The CT device may include a radiation source configured to emit radiation beams toward the object and a detector configured to detect radiation beams (e.g., x-ray photons, gamma-ray photons) emitted from an imaging region of the CT device. The radiation source and the detector may be arranged oppositely. The imaging region of the CT device may be formed between the radiation source and the detector. The radiation device 710 may be a similar device as the radiation device 110 in FIG. 1, and relevant descriptions are not repeated here.

The projection device 730 may be configured to project reference image data 731 associated with the object to a target position. The reference image data 731 may provide guidance information associated with the medical procedure for the object. The guidance information may include position and/or posture information that the object needs to maintain on a table 740 of the medical system 700. For example, the reference image data 731 may be a three-dimensional (3D) human body image. Merely by way of example, the posture information in the 3D human body image may include lying (e.g., lying on the back, lying on the stomach, lying on the left, lying on the right), standing, raising arms, raising legs, and/or turning head, etc. In some embodiments, the posture information may be previously determined and stored in a storage device (e.g., the storage device 220). For example, the processing device 720 may previously determine the posture information based on the requirements of the medical procedure and/or a diagnosis result of the object. In some embodiments, the target position may be located on or above the table 740 of the medical system 700. The object may lie on the table 740 of the medical system 700 in a posture by himself (or herself) according to the posture information provided by the reference image data 731.

In some embodiments, the projection device 730 may include a holographic projection device, a virtual reality device, an augmented reality device, or the like, or any combination thereof. In some embodiments, the radiation device 710 may be contained in a shielded room. The projection device 730 may be arranged on the ceiling of the shielded room or an upper part of the radiation device 710 by a rigid rod-shaped structure. A projection direction of the projection device 730 may be perpendicular to a plane (e.g., a surface of the table 740) where the target position is located.

The processing device 720 may be in communication with the radiation device 710 and the projection device 730 and configured to control at least one of the radiation device 710 or the projection device 730. For example, a user (e.g., a doctor, a radiologist, a nurse) may control the radiation device 710 and/or the projection device 730 by the processing device 720. As another example, the user may control the projection device 730 to project reference image data 731, and then the object may lie on the table 740 of the medical system 700 by himself (or herself) according to the reference image data 731. Therefore, without entering the shielded room that contains the radiation device 710, the user may interact with the object without contact to remotely guide the object to lie on the table 740 of the medical system 700 in a required posture, which may reduce unnecessary radiation suffered by the user, reduce or even completely avoid the probability of the user being infected by the object, and avoid or reduce the user walking back and forth between the shielded room and a control room of the processing device 720, thereby improving work efficiency and the occupational safety of the user. In some embodiments, the processing device 720 may include an application program configured to communicate with the radiation device and the projection device. The processing device 720 may be a similar device as the processing device 120 in FIG. 1, and relevant descriptions are not repeated here.

When a user (e.g., a doctor, a radiologist, a nurse) is ready to perform a medical procedure (e.g., observation, treatment) on an object (e.g., a patient) using the radiation device 710, the user may enter the requirements of the medical procedure and/or the diagnosis result of the object into the processing device 720 or obtain the requirements of the medical procedure and/or the diagnosis result of the object from other medical systems in communication with medical system 700, and then start (or trigger) the projection device 730.

In some embodiments, the projection device 730 may be controlled manually or automatically. For example, the user may manually start (or trigger) the projection device 730 by the application program of the processing device 720. As another example, the processing device 720 may include a trigger component. The user may manually start (or trigger) the projection device 730 by the trigger component. Specifically, the user may operate the application program or the trigger component on a display interface of the processing device 720 by clicking, sliding, etc. When the application program or the trigger component is operated, the processing device 720 may start (or trigger) the projection device 730 to project reference image data 731. As a further example, the processing device 720 may obtain a current position of the table 740 of the medical system 700. When the current position of the table 740 reaches a preset position, the processing device 720 may automatically start (or trigger) the projection device 730 to project reference image data 731. The preset position may be default settings of the medical system 700 or may be adjustable under different situations.

In some embodiments, the processing device 720 may obtain characteristic information of the object from the requirements of the medical procedure and/or the diagnosis result of the object. Merely by way of example, the characteristic information may include age, height, weight, gender of the object, etc. According to the characteristic information of the object and a trained model for image data construction, the processing device 720 may determine the reference image data 731. The trained model for image data construction may include a neural network model or other machine learning models. The processing device 720 may input the characteristic information of the object into the trained model for image data construction and determine the reference image data 731 based on an output of the trained model for image data construction. The reference image data 731 that is determined based on the characteristic information of the object may be more matched with the characteristic of the object, thereby providing the object with more suitable reference image data 731.

In some embodiments, the processing device 720 may determine (or generate) projection information based on the requirements of the medical procedure and/or the diagnosis result of the object. The projection information may include projection data and/or a projection angle associated with the reference image data 731. In some embodiments, the projection angle may be determined by the processing device 720 according to actual projection requirements. In some embodiments, the projection angle may be determined by the user and configured in the projection device 730 in advance. In some embodiments, the projection data refers to data (e.g., data related to position and/or posture that the object needs to maintain on the table 740 of the medical system 700) used to generate the reference image data 731. Further, the processing device 720 may send a projection instruction and the projection information to the projection device 730. After receiving the projection instruction and the projection information, the projection device 730 may generate the reference image data 731 based on the projection data. Further, the projection device 730 may project the reference image data 731 based on the projection instruction and the projection angle. In some embodiments, the projection instruction may include the projection information. The projection device 730 may generate the reference image data 731 based on the projection instruction. In some embodiments, the projection device 730 may include a receiver, a reconstruction component, and a projection component. The receiver may be configured to receive the projection instruction and the projection information. The reconstruction component may be configured to generate the reference image data 731 based on the projection data. The projection component may be configured to project the reference image data 731 based on the projection instruction and the projection angle. In some embodiments, the projection component may be a lens with a projection image function.

After the reference image data 731 is projected to the target position, the object may lie on the table 740 of the medical system 700 in a posture according to the posture information provided by the reference image data 731. For example, if the posture information includes lying flat with legs bent, the object may lie flat on the table 740 of the medical system 700 and bend both legs. After that, the user may control the processing device 720 to move the object into a detection region (e.g., the imaging region of the CT device) of the radiation device 710. Further, the processing device 720 may send a control instruction to the radiation device 710. After receiving the control instruction, the radiation device 710 may perform the medical procedure (e.g., observation, treatment) on the object. In some embodiments, the projection device 730 may automatically stop the projection after projecting the reference image data 731 for a preset time. The preset time may be default settings (e.g., 15 seconds) of the medical system 700 or may be adjustable under different situations.

In some embodiments, the processing device 720 may determine a target region where a target part of the object that needs to be performed the medical procedure is located based on the reference image data 731. The target part of the object may include one or more organs (e.g., a tumor, a cancer-ridden organ, or a non-cancerous target of radiation therapy) that need observation and/or treatment. The processing device 720 may determine the target region based on a region of the target part of the object on the reference image data 731 and the target position, and then perform the medical procedure on the target region, which may realize the positioning of the target region where the target part of the object is located, thereby improving the accuracy of performing the medical procedure.

Figure 8:
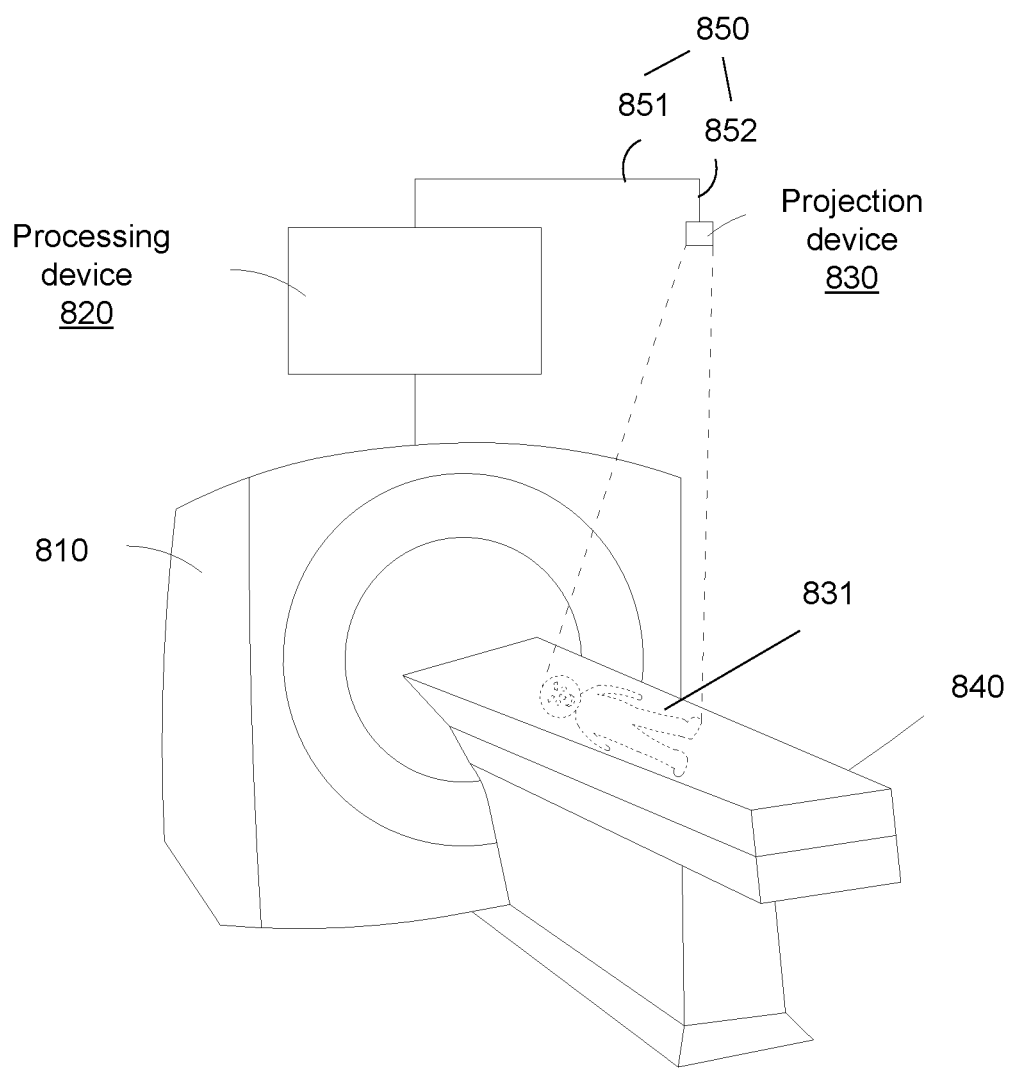
FIG. 8 is a schematic diagram illustrating an exemplary medical system according to some embodiments of the present disclosure.

FIG. 8 is a schematic diagram illustrating an exemplary medical system according to some embodiments of the present disclosure. As illustrated in FIG. 8, the medical system 800 may include a radiation device 810, a processing device 820, and a projection device 830. The radiation device 810, the processing device 820, and the projection device 830 may respectively be similar as the radiation device 710, the processing device 720, and the projection device 730 in FIG. 7, and relevant descriptions are not repeated here.

As illustrated in FIG. 8, the medical system 800 may further include a table 840. The table 840 may be configured to move an object placed on the table 840 to a target region for performing the medical procedure. The projection device 830 may be arranged above the table 840 and rotated within a preset angle range. The preset range may be set according to actual needs. A projection direction of the reference image data 831 projected by the projection device 830 may be perpendicular to a surface of the table 840 for placing the object. In some embodiments, as illustrated in FIG. 8, a support structure 850 may be provided between the projection device 830 and the table 840. The support structure 850 may include a support arm 851 and a rotating rod 852. The support arm 851 may be arranged on the top of the radiation device 810. One end of the rotating rod 852 may be rotatably arranged on the support arm 851, and the other end of the rotating rod 852 may be connected with the projection device 830. The rotating rod 852 may drive the projection device 830 to rotate at any degree (e.g., 90 degrees) around the support arm 851. The support arm 851 may extend along a length of the table 840, and the longest extension length of the support arm 851 may be less than the length of the support arm 851. The rotating rod 852 may extend and contract in a direction perpendicular to the extension direction of the support arm 851.

A target position of the projection device 830 to project reference image data 831 may be located on or above an upper surface of the table 840. For example, as illustrated in FIG. 8, the projection device 830 may project the reference image data 831 on the upper surface of the table 840, so that the reference image data 831 may be similar to that placed on the upper surface of the table 840. As another example, the projection device 830 may project the reference image data 831 into a space at a certain distance (e.g., 1 meter) from the upper surface of the table 840, so that the object may more clearly view posture information provided by the reference image data 831. In this case, after lying on the table 840, the object may adjust his/her position and/or posture by observing the reference image data 831 in the space above the table 840 to make his/her position and/or posture more accurate, which reduces the time wasted by a user (e.g., a doctor, a radiologist, a nurse) telling the object how to adjust his/her position and/or posture, thereby improving the efficiency of the medical system 800.

Figure 9:
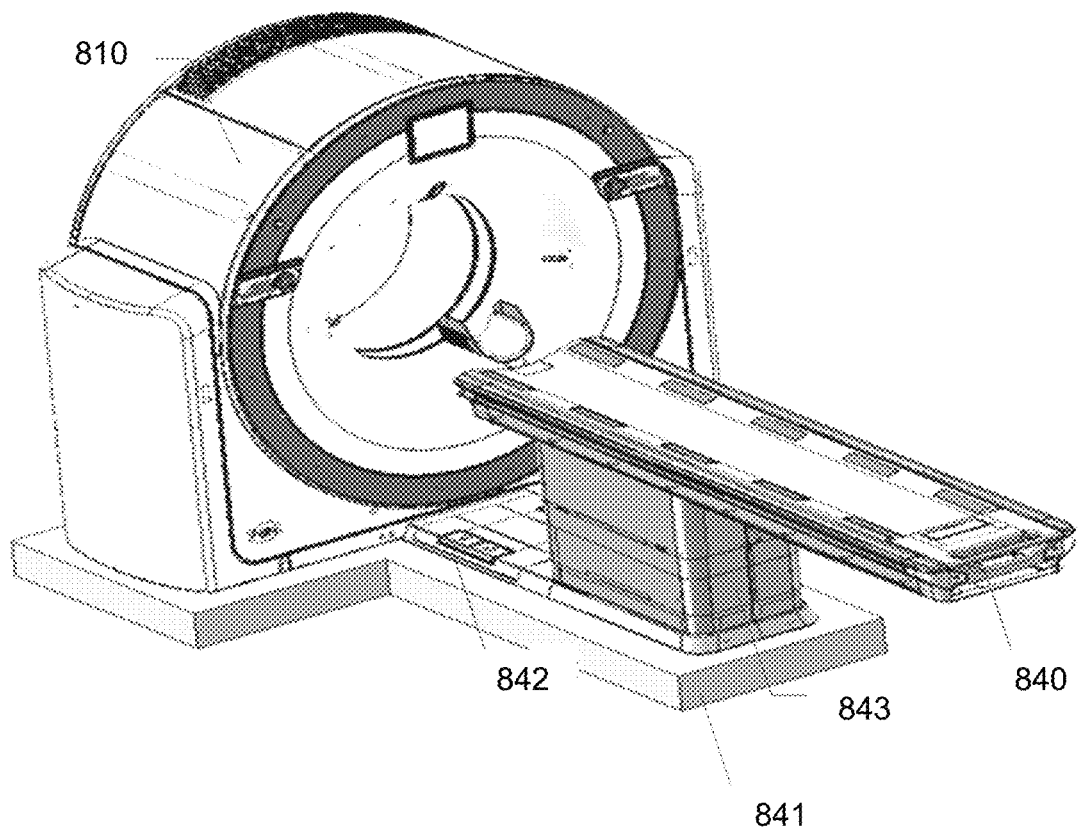
FIG. 9 is a schematic diagram illustrating an exemplary table according to some embodiments of the present disclosure.

In some embodiments, the table 840 may be controlled by the processing device 820 to move vertically and/or horizontally. FIG. 9 is a schematic diagram illustrating an exemplary table according to some embodiments of the present disclosure. As illustrated in FIG. 9, a sliding rail 842 is provided on a base 841 supporting the table 840. The processing device 820 may control the table 840 to move horizontally through the sliding rail 842. A support column 843 supporting the table 840 may be vertically telescopic. The processing device 820 may control the support column 843 to perform telescopic movement to drive the table 840 to move vertically.

Figure 10:
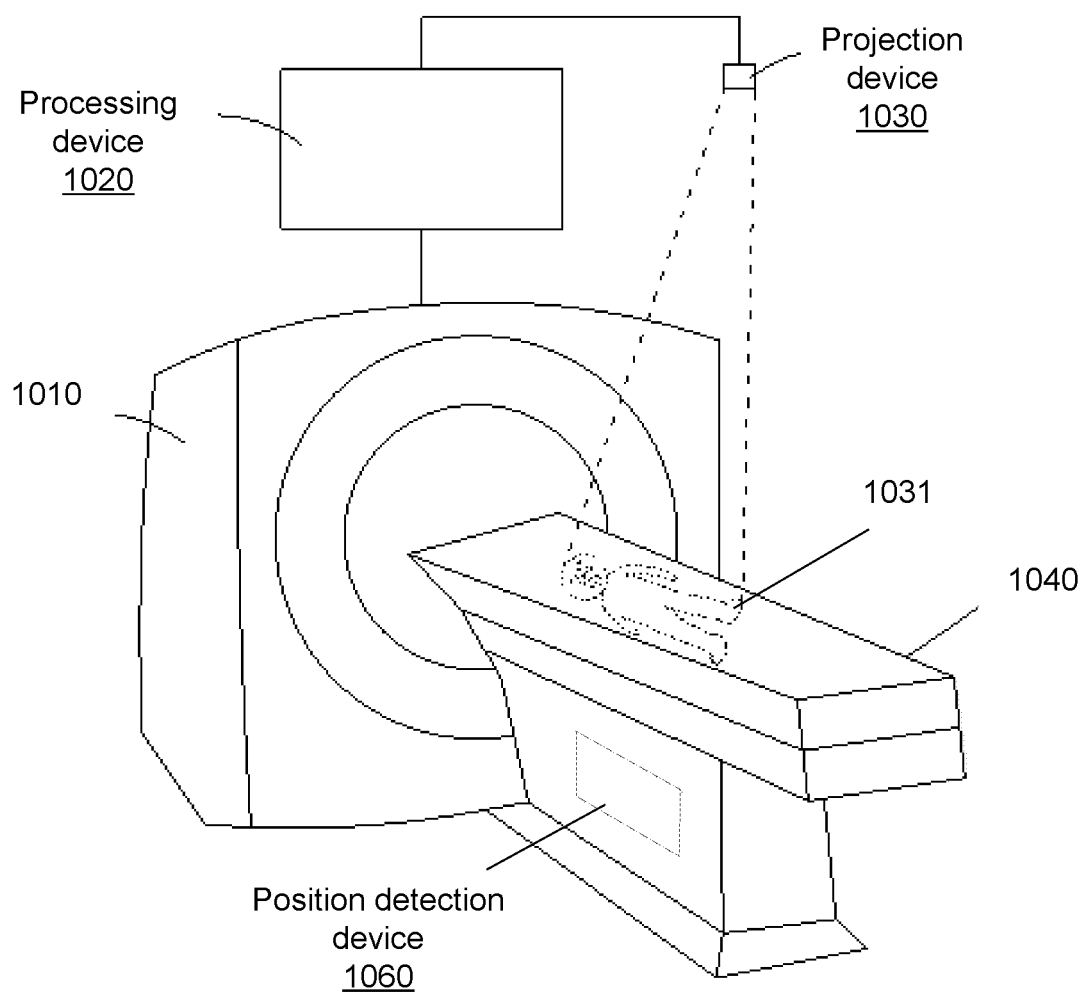
FIG. 10 is a schematic diagram illustrating an exemplary medical system according to some embodiments of the present disclosure.

FIG. 10 is a schematic diagram illustrating an exemplary medical system according to some embodiments of the present disclosure. As illustrated in FIG. 10, the medical system 1000 may include a radiation device 1010, a processing device 1020, a projection device 1030, and a table 1040. The radiation device 1010, the processing device 1020, the projection device 1030, and the table 1040 may respectively be similar as the radiation device 810, the processing device 820, the projection device 830, and the tale 840 in FIG. 8, and relevant descriptions are not repeated here.

As illustrated in FIG. 10, the medical system 1000 may further include a position detection device 1060. The position detection device 1060 may be arranged in the table 1040 or a surface of the table 1040. The position detection device 1060 may be in communication with the processing device 1020. The position detection device 1060 may be configured to detect a position of the table 1040. Merely by way of example, the position detection device 1060 may include a position sensor, a displacement sensor, etc. When the table 1040 moves, the position detection device 1060 may detect a current position of the table 1040 in real time. The current position may be represented by three-dimensional coordinates. Further, the position detection device 1060 may transmit the position of the table 1040 to the processing device 1020. According to the position of the table 1040, the processing device 1020 may be configured to determine whether the projection device 1030 is triggered to project reference image data 1031. Specifically, the processing device 1020 may determine whether the current position of the table 1040 meets the requirements based on the position of the table 1040. For example, when the projection device 1030 projects the reference image data 1031, the object is not yet on the table 1040. Therefore, the height of the table 1040 should be a relatively low height so that the object may easily reach the bed. The processing device 1020 may determine whether a current height of the table 1040 is larger than a preset height based on the position of the table 1040. The preset height may be default settings of the medical system 1000 or may be adjustable under different situations. If the current height of the table 1040 is less than the preset height, the processing device 1020 may determine that the current position of the table 1040 meets the requirements and trigger the projection device 1030 to project the reference image data 1031. If the current height of the table 1040 is larger than the preset height, the processing device 1020 may determine that the current position of the table 1040 does not meet the requirements and adjust the height of the table 1040 until the height of the table 1040 is less than the preset height.

In some embodiments, according to the current position of the table 1040 and a position, on the table 1040, of a target part of the object that needs to be performed the medical procedure, the processing device 1020 may determine a moving direction and distance of the table 1040 that carries the object into a detection region of the radiation device 1010 for performing the medical procedure. Further, according to the moving direction and distance, the processing device 1020 may control the table 1040 to move into the detection region of the radiation device 1010.

Figure 11:
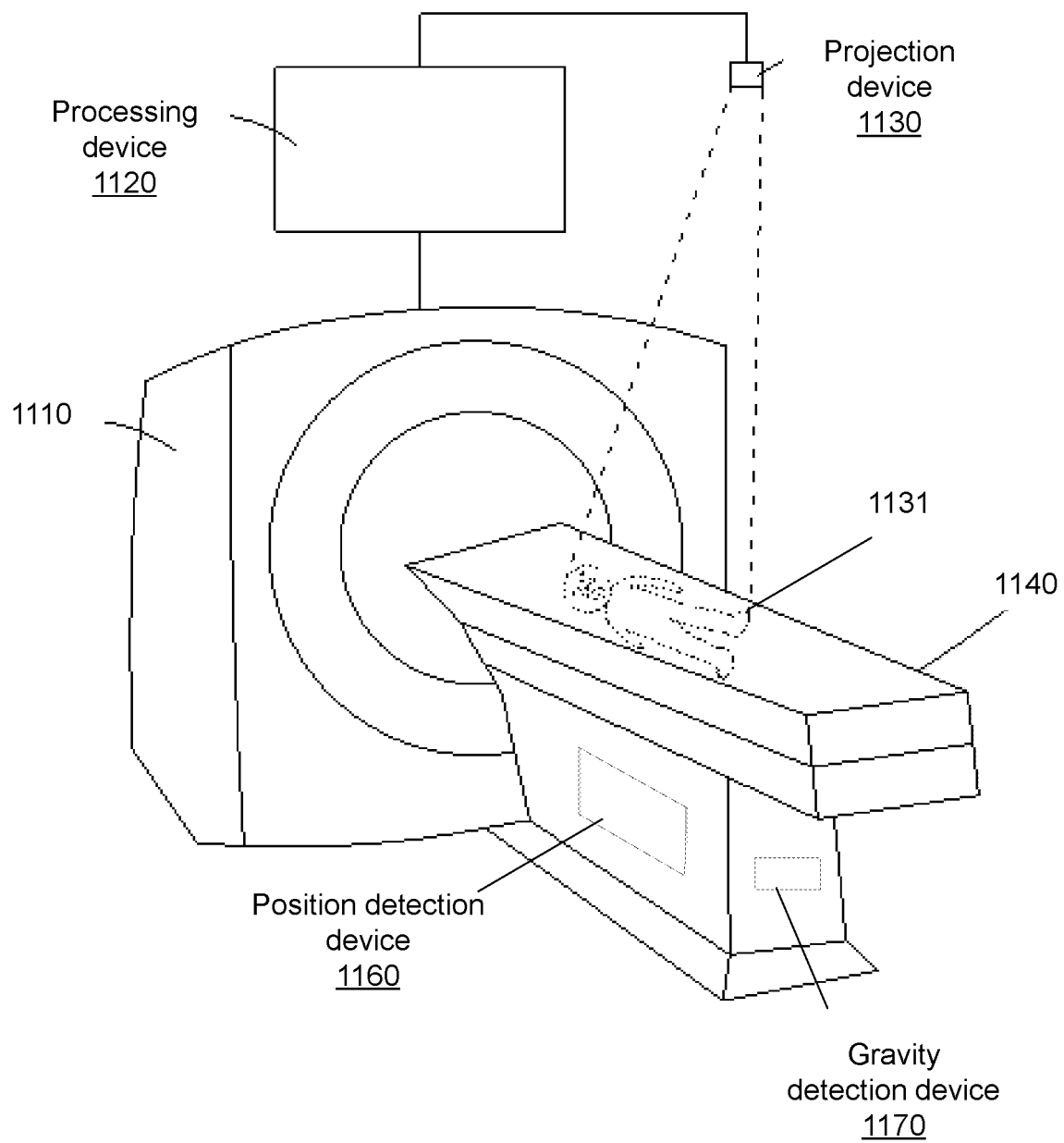
FIG. 11 is a schematic diagram illustrating an exemplary medical system according to some embodiments of the present disclosure.

FIG. 11 is a schematic diagram illustrating an exemplary medical system according to some embodiments of the present disclosure. As illustrated in FIG. 11, the medical system 1100 may include a radiation device 1110, a processing device 1120, a projection device 1130, and a table 1140. The radiation device 1110, the processing device 1120, the projection device 1130, and the table 1140 may respectively be a similar device as the radiation device 810, the processing device 820, the projection device 830, and the tale 840 in FIG. 8, and relevant descriptions are not repeated here.

As illustrated in FIG. 11, the medical system 1100 may further include a gravity detection device 1170. The gravity detection device 1170 may be arranged in the table 1140 or a surface of the table 1140. The gravity detection device 1170 may be in communication with the processing device 1120. Merely by way of example, the gravity detection device 1170 may include a force sensor. The gravity detection device 1170 may be configured to detect a weight carried by the table 1140 and transmit the weight to the processing device 1120. The processing device 1120 may be configured to determine whether the projection device 1130 is triggered to project the reference image data 1131 based on the weight carried by the table 1140. Specifically, the processing device 1120 may determine whether the object is already on the table 1140 based on the weight carried by the table 1140. If the object is not on the table 1140, the processing device 1120 may trigger the projection device 1130 to project the reference image data 1131. If the object is already on the table 1140, the processing device 1120 may control the projection device 1130 to stop projecting the reference image data 1131.

In some embodiments, as illustrated in FIG. 11, the medical system 1100 may further include a position detection device 1160. The position detection device 1160 may be similar as the position detection device 1060 in FIG. 10, and relevant descriptions are not repeated here.

Figure 12:
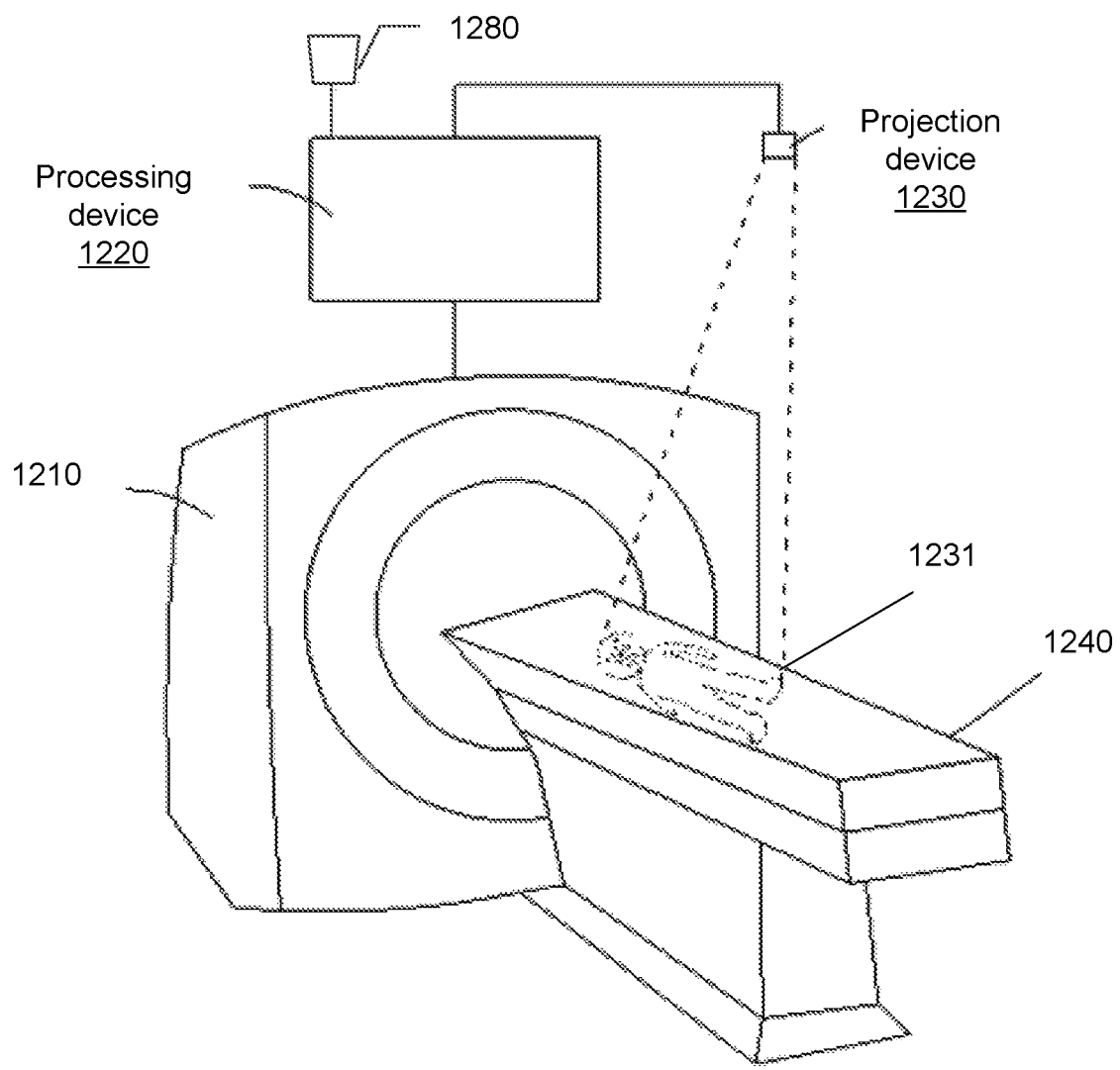
FIG. 12 is a schematic diagram illustrating an exemplary medical system according to some embodiments of the present disclosure.

FIG. 12 is a schematic diagram illustrating an exemplary medical system according to some embodiments of the present disclosure. As illustrated in FIG. 12, the medical system 1200 may include a radiation device 1210, a processing device 1220, a projection device 1230, and a table 1240. The radiation device 1210, the processing device 1220, the projection device 1230, and the table 1240 may respectively be a similar device as the radiation device 810, the processing device 820, the projection device 830, and the tale 840 in FIG. 8, and relevant descriptions are not repeated here.

As illustrated in FIG. 12, the medical system 1200 may further include a voice device 1280. The voice device 1280 may be in communication with the processing device 1220. In some embodiments, the voice device 1280 may be an independent device and arranged near the processing device 1220, the radiation device 1210, or the table 1240. In some alternative embodiments, the voice device 1280 may be integrated into the processing device 1220 or the radiation device 1210. Merely by way of example, the voice device 1280 may include a microphone, a speaker, etc. In some embodiments, the voice device 1280 may be configured to interact with the object. For example, the voice device 1280 may be broadcast guidance information provided by reference image data 1231 projected by the projection device 1230. As described in connection with FIG. 7, the guidance information may include a position and/or posture that the object needs to maintain on the table 1240 of the medical system 1200. Specifically, the voice device 1280 may receive the guidance information from the processing device 1220 and broadcast the guidance information, which allows the object to know the position and/or posture more clearly, thereby improving the efficiency of the medical system 1200. In some embodiments, the voice device 1280 may broadcast the guidance information before, during, or after the projection device 1230 projects the reference image data 1231, which is not limited herein.

In some embodiments, the medical system 1200 may further include a position detection device and/or a gravity detection device (not shown). The position detection device and the gravity detection device may respectively be a similar device as the position detection device 1060 in FIG. 10 and the gravity detection device 1170 in FIG. 11, and relevant descriptions are not repeated here.

Figure 13:
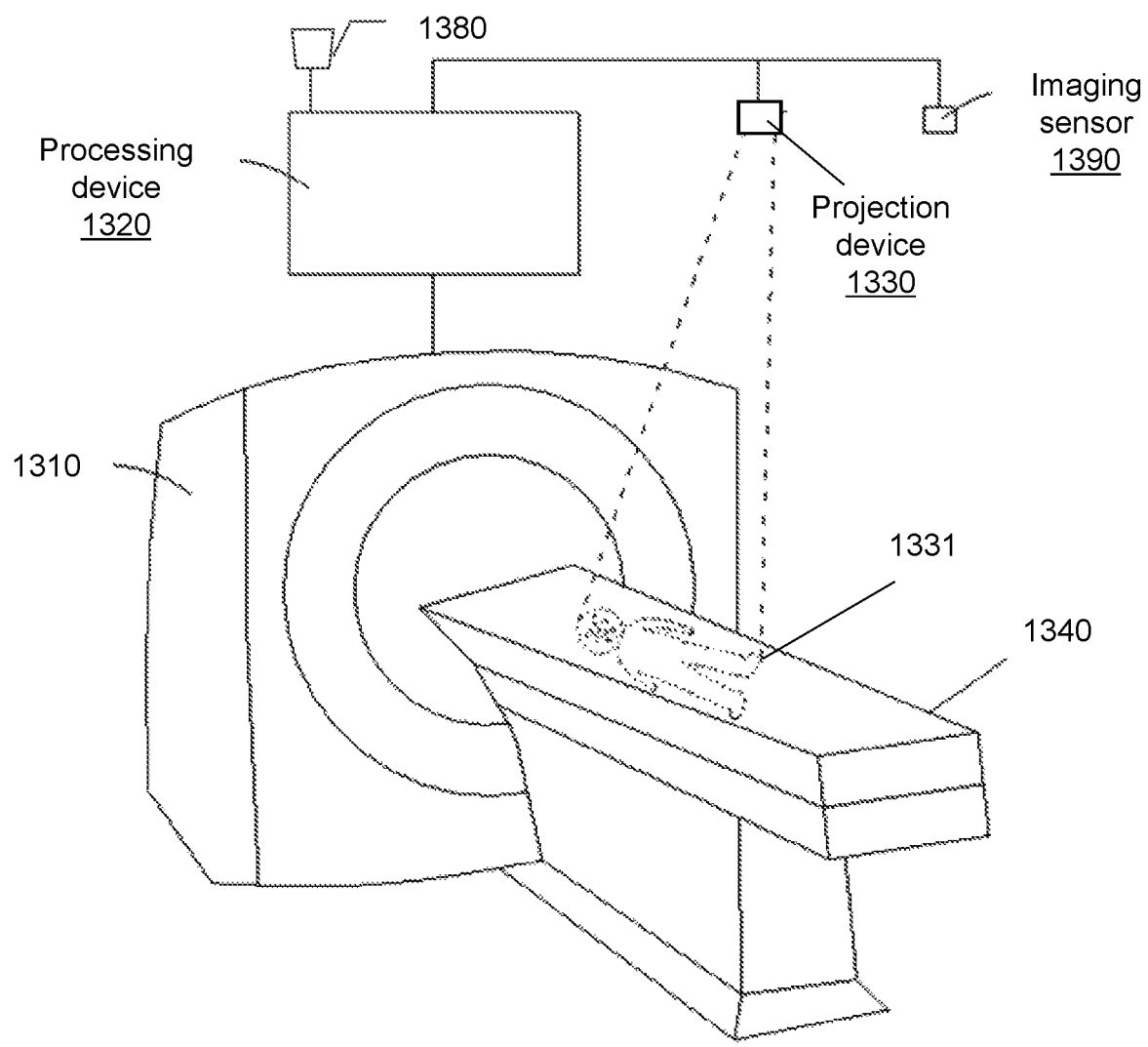
FIG. 13 is a schematic diagram illustrating an exemplary medical system according to some embodiments of the present disclosure.

FIG. 13 is a schematic diagram illustrating an exemplary medical system according to some embodiments of the present disclosure. As illustrated in FIG. 13, the medical system 1300 may include a radiation device 1310, a processing device 1320, a projection device 1330, and a table 1340. The radiation device 1310, the processing device 1320, the projection device 1330, and the table 1340 may respectively be a similar device as the radiation device 810, the processing device 820, the projection device 830, and the tale 840 in FIG. 8, and relevant descriptions are not repeated here.

As illustrated in FIG. 13, the medical system 1300 may include an imaging sensor 1390. The imaging sensor 1390 may be in communication with the processing device 1320. After the object lies on the table 1340 according to posture information provided by the reference image data 1331, in order to confirm whether the position and/or the posture of the object is accurate, the processing device 1320 may direct the imaging sensor 1390 to capture one or more images associated with the object. Further, the imaging sensor 1390 may transmit the one or more images associated with the object to the processing device 1320.

The processing device 1320 may be configured to notify, by a voice device 1380, the object to perform positioning correction based on a comparison of the one or more images associated with the object and reference image data 1331 projected by the projection device 1330. In some embodiments, the processing device 1320 may compare whether the position and/or the posture of the object is consistent with that in the reference image data 1331. If the position and/or the posture of the object is not consistent with that in the reference image data 1331, the processing device 1320 may obtain correction information for correcting the position and/or the posture of the object. Further, the processing device 1320 may transmit the correction information to the voice device 1380, and the voice device 1380 may broadcast the correction information to notify the object to perform the positioning correction based on the correction information, which allows the object to perform the positioning correction on their own without requiring on-site guidance. In some embodiments, the imaging sensor 1390 may capture the one or more images associated with the object at a certain time interval and transmit the one or more images to the processing device 1320 for comparison until the position and/or the posture of the object is consistent with that in the reference image data 1331.

In some embodiments, after receiving the one or more images associated with the object, the processing device 1320 may display the one or more images on a display interface of the processing device 720 for a user (e.g., a doctor, a radiologist, a nurse) to view. After viewing the one or more images, the user may input a voice telling the object how to perform the positioning correction into the voice device 1380 to tell the object how to perform the positioning correction. In this case, the user does not need to enter a shielded room that contains the radiation device 1310 to guide the object to perform the positioning correction, which may reduce unnecessary radiation suffered by the user, thereby improving work efficiency and the occupational safety of the user. More descriptions of the imaging sensor may be found elsewhere in the present disclosure (e.g., FIG. 4 and the description thereof).

In some embodiments, the voice device 1380 illustrated in FIG. 13 may be a similar device as the voice device 1280 illustrated in FIG. 12, and relevant descriptions are not repeated here. In some embodiments, the medical system 1300 may further include a position detection device and/or a gravity detection device (not shown). The position detection device and the gravity detection device may respectively be a similar device as the position detection device 1060 in FIG. 10 and the gravity detection device 1170 in FIG. 11, and relevant descriptions are not repeated here.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A computer-readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer-readable signal medium may be any computer-readable medium that is not a computer-readable storage medium and that may communicate, propagate, or transport a program for use by or in connection with an instruction performing system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer, and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A medical system, comprising:
   an imaging sensor;
   a positioning lamp;
   at least one storage device including a set of instructions; and
   at least one processor in communication with the at least one storage device, wherein when executing the set of instructions, the at least one processor is directed to perform operations including:
   determining a working phase of the medical system, the working phase of the medical system including at least one of a positioning phase, a scanning phase, or a scanning completion phase;
   determining a position of a target portion of an object in the medical system based on one or more images associated with the object captured by the imaging sensor; and
   controlling an operation of the positioning lamp of the medical system based on the working phase of the medical system and the position of the target portion of the object in the medical system.

2. The medical system of claim 1, wherein the determining the working phase of the medical system includes:
   obtaining workflow information of the medical system in a current medical procedure of an object; and
   determining the working phase of the medical system based on the workflow information of the medical system in the current medical procedure of the object.

3. The medical system of claim 1, wherein the determining the position of the target portion of the object in the medical system based on the one or more images associated with the object captured by the imaging sensor includes:
   identifying the target portion of the object from the one or more images associated with the object;
   obtaining the position of the target portion of the object in a first coordinate system of the imaging sensor or the one or more images; and
   determining the position of the target portion of the object in a second coordinate system of the medical system based on the position of the target portion of the object in the first coordinate system of the imaging sensor or the one or more images.

4. The medical system of claim 1, wherein the controlling the operation of the positioning lamp of the medical system based on the working phase of the medical system and the position of the target portion of the object in the medical system includes:
   determining whether the working phase of the medical system is the positioning phase; and
   in response to determining that the working phase of the medical system is the positioning phase, controlling the operation of the positioning lamp of the medical system based on an irradiation region of the positioning lamp and the position of the target portion of the object in the medical system.

5. The medical system of claim 4, further including:
   a table, and
   the determining whether the working phase of the medical system is the positioning phase includes:
   obtaining the one or more images associated with the object captured by the imaging sensor, the one or more images including one or more first images of the object and one or more second images of the object and a target object;
   determining whether the object is located on the table of the medical system based on the one or more first images of the object; in response to determining that the object is located on the table, determining whether a distance between the table and the target object is less than or equal to a preset threshold based on the one or more second images; and in response to determining that the distance between the table and the target object is less than or equal to the preset threshold, determining that the working phase of the medical system is the positioning phase.

6. The medical system of claim 4, wherein the controlling the operation of the positioning lamp of the medical system based on the irradiation region of the positioning lamp and the position of the target portion of the object in the medical system includes:

determining whether the position of the target portion of the object is within the irradiation region of the positioning lamp;

in response to determining that the position of the target portion of the object is not within the irradiation region of the positioning lamp, controlling the positioning lamp of the medical system to be turned on; and in response to determining that the position of the target portion of the object is within the irradiation region of the positioning lamp, controlling the positioning lamp of the medical system to keep turned off.

7. The medical system of claim 6, further including:
a table, and
in response to determining that the position of the target portion of the object is not within the irradiation region of the positioning lamp, the controlling the positioning lamp of the medical system to be turned on includes:
controlling the positioning lamp of the medical system to be turned on based on a position or a movement state of the table of the medical system.

8. The medical system of claim 1, wherein the controlling the operation of the positioning lamp of the medical system based on the working phase of the medical system and the position of the target portion of the object in the medical system includes:
in response to determining that the working phase of the medical system is not the positioning phase, controlling the positioning lamp of the medical system to keep turned off.

9. The medical system of claim 1, further including:
a radiation device configured to perform a medical procedure on an object by emitting radiation beams toward the object; and
a projection device configured to project reference image data associated with the object to a target position, the reference image data providing guidance information associated with the medical procedure on the object;
wherein the at least one processor is in communication with the radiation device and the projection device and configured to control at least one of the radiation device or the projection device.

10. The medical system of claim 9, further including:
a table configured to move the object placed on the table to a target region for performing the medical procedure, a projection direction of the reference image data projected by the projection device is perpendicular to a surface of the table for placing the object.

11. The medical system of claim 10, further including:
a position detection device in communication with the at least one processor, wherein
the position detection device is configured to detect a position of the table, and
the at least one processor is configured to determine whether the projection device is triggered to project the reference image data based on the position of the table.

12. The medical system of claim 10, further including:
a gravity detection device in communication with the at least one processor, wherein
the gravity detection device is configured to detect a weight carried by the table, and
the at least one processor is configured to determine whether the projection device is triggered to project the reference image data based on the weight carried by the table.

13. The medical system of claim 9, further including:
a table; and
a voice device configured to broadcast the guidance information provided by the reference image data projected by the projection device, the guidance information including position and posture information that the object needs to maintain on the table of the medical system.

14. The medical system of claim 13, wherein the imaging sensor is in communication with the at least one processor, wherein
the imaging sensor is configured to capture the one or more images associated with the object, and
the at least one processor is configured to notify, by the voice device, the object to perform a positioning correction based on a comparison of the one or more images associated with the object and the reference image data.

15. The medical system of claim 9, wherein the at least one processor includes a trigger component configured to trigger the projection device to project the reference image data to the target position.

16. The medical system of claim 9, wherein the at least one processor is further configured to:
obtain characteristic information of the object, the characteristic information including at least one of age, height, weight, or gender of the object; and
determine the reference image data based on the characteristic information of the object and a trained image data construction model.

17. The medical system of claim 9, wherein the projection device is further configured to:
receive a projection instruction and projection information from the at least one processor, the projection information including projection data and a projection angle associated with the reference image data;
generate the reference image data based on the projection data; and
project the reference image data based on the projection instruction and the projection angle.

18. The medical system of claim 9, wherein the at least one processor is further configured to determine a target region, where a target part of the object that needs to be performed the medical procedure is located based on the reference image data.

19. A method for controlling a medical system, wherein:
the medical system includes a table configured to move an object placed on the table and a gantry configured to form a cavity, the gantry including a positioning lamp, the method includes:
controlling the positioning lamp to be turned on;
controlling the table that carries the object to move along a long axis of the cavity to enter the cavity;

determining a position of a target portion of the object in the medical system;

determining whether a distance between the position of the target portion of the object and an irradiation region of the positioning lamp is less than a distance threshold; and in response to determining that the distance between the position of the target portion of the object and the irradiation region of the positioning lamp is less than the distance threshold, controlling the positioning lamp of the medical system to be turned off.

20. The method of claim 19, further including:

a radiation device configured to perform a medical procedure on the object by emitting radiation beams toward the object; and a projection device configured to project reference image data associated with the object to a target position, the reference image data providing guidance information associated with the medical procedure for the object; and at least one processor in communication with the radiation device and the projection device, the at least one processor being configured to control at least one of the radiation device or the projection device.

* * * * *